(12) United States Patent
Feke

(10) Patent No.: US 9,560,292 B2
(45) Date of Patent: Jan. 31, 2017

(54) FRAME-SEQUENTIAL MULTIWAVELENGTH IMAGING SYSTEM AND METHOD

(71) Applicant: Bruker Biospin Corporation, Billerica, MA (US)

(72) Inventor: Gilbert D. Feke, Durham, CT (US)

(73) Assignee: Bruker Biospin Corporation, Billerica, MA (US)

( * ) Notice: Subject to any disclaimer, the term of this patent is extended or adjusted under 35 U.S.C. 154(b) by 490 days.

(21) Appl. No.: 14/348,448

(22) PCT Filed: Sep. 27, 2012

(86) PCT No.: PCT/US2012/057407
§ 371 (c)(1),
(2) Date: Mar. 28, 2014

(87) PCT Pub. No.: WO2013/049264
PCT Pub. Date: Apr. 4, 2013

(65) Prior Publication Data
US 2014/0240468 A1 Aug. 28, 2014

Related U.S. Application Data

(60) Provisional application No. 61/540,229, filed on Sep. 28, 2011.

(51) Int. Cl.
*H04N 13/04* (2006.01)
*H04N 5/33* (2006.01)
(Continued)

(52) U.S. Cl.
CPC ............... *H04N 5/33* (2013.01); *A61B 1/0638* (2013.01); *A61B 1/0646* (2013.01);
(Continued)

(58) Field of Classification Search
USPC ............................................. 348/47, 77, 164
See application file for complete search history.

(56) References Cited

U.S. PATENT DOCUMENTS 5,822,222 A * 10/1998 Kaplinsky ................. G01J 5/60
250/316.1
8,391,943 B2 * 3/2013 Li ....................... A61B 5/02416
600/323

(Continued)

FOREIGN PATENT DOCUMENTS

| CN | 101366632 | 2/2009 |
|----|-----------|--------|
| WO | 2008153014 | 12/2008 |

OTHER PUBLICATIONS

European Search Report dated Jun. 9, 2015.

*Primary Examiner* — Gims Philippe
(74) *Attorney, Agent, or Firm* — O'Shea Getz P.C.

(57) ABSTRACT

A frame-sequential multiwavelength imaging system comprises a wavelength switching device for producing a repeated series of different wavelength profiles, a detector for detecting the dynamic scene and a signal processing unit for synthesizing a dynamic multiwavelength image of the dynamic scene. The signal processing unit may comprise at least one input device at least one logic device and at least one output device. The system can be used in a method to perform multiwavelength imaging of a dynamic scene, typically for surgical purposes.

20 Claims, 28 Drawing Sheets

(51) Int. Cl.
    *A61B 1/06*         (2006.01)
    *H04N 7/18*         (2006.01)
    *H04N 13/02*       (2006.01)
    *A61B 5/00*         (2006.01)
    *A61B 5/1455*      (2006.01)
    *A61B 5/06*         (2006.01)

(52) U.S. Cl.
    CPC .......... *A61B 1/0669* (2013.01); *A61B 5/0059* (2013.01); *A61B 5/14551* (2013.01); *H04N 7/18* (2013.01); *H04N 13/0239* (2013.01); *A61B 5/0046* (2013.01); *A61B 5/0073* (2013.01); *A61B 5/06* (2013.01); *A61B 2505/05* (2013.01); *F04C 2270/041* (2013.01)

(56) References Cited

U.S. PATENT DOCUMENTS

| | | | |
|---|---|---|---|
| 8,475,506 B1 * | 7/2013 | Bendett | A61N 5/0622 607/88 |
| 8,838,211 B2 * | 9/2014 | Melendez | A61B 5/00 600/300 |
| 9,134,243 B2 * | 9/2015 | Wilson | A61B 5/0059 |
| 2003/0085338 A1 | 5/2003 | Hall et al. | |
| 2003/0139667 A1 | 7/2003 | Hewko et al. | |
| 2004/0092824 A1 | 5/2004 | Stamnes et al. | |
| 2009/0216098 A1 | 8/2009 | Stranc et al. | |
| 2010/0026995 A1 | 2/2010 | Merritt et al. | |
| 2012/0293790 A1 | 11/2012 | Frankenberger et al. | |

\* cited by examiner

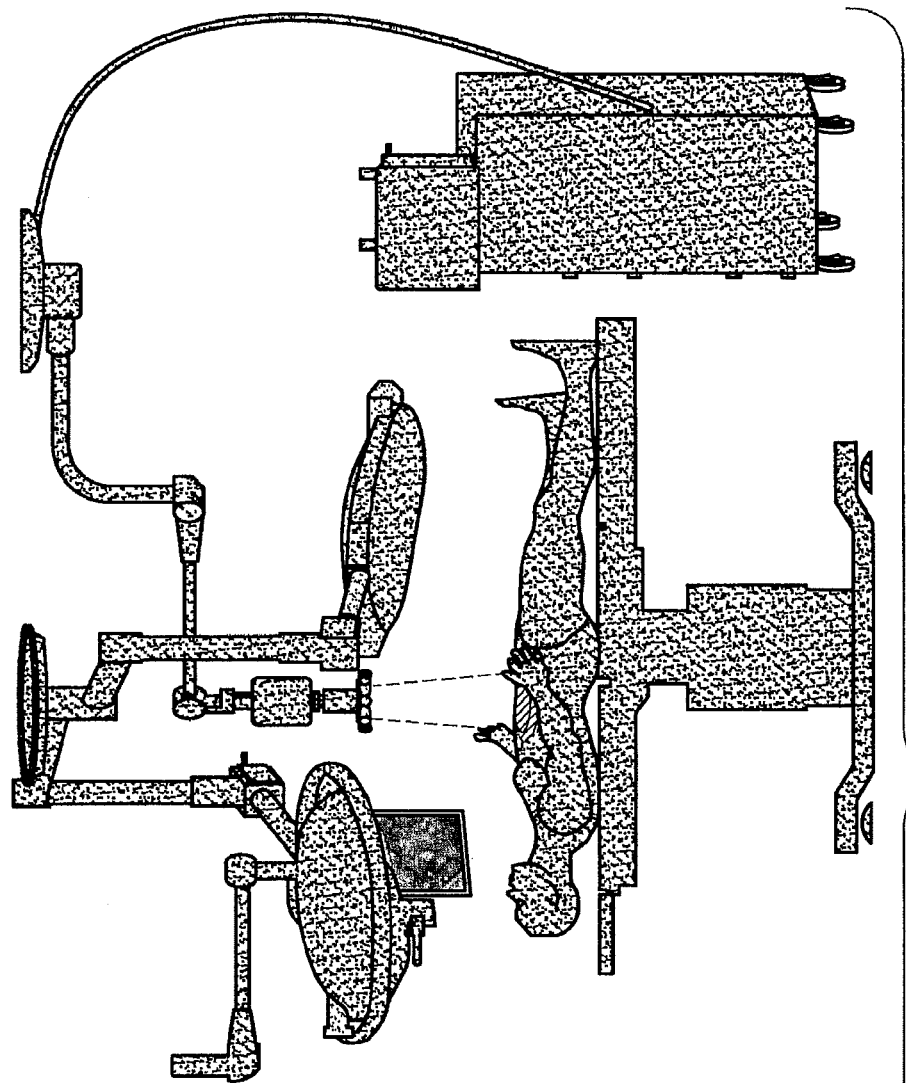
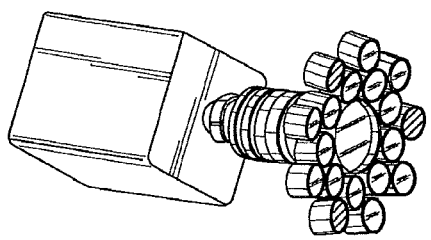
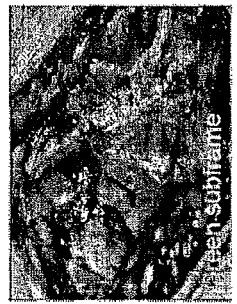
Monochrome Exposure under green illumination
Real time:
0.001 sec to 0.002 sec
(1/40th of 25 fps video frame)
FIG. 12

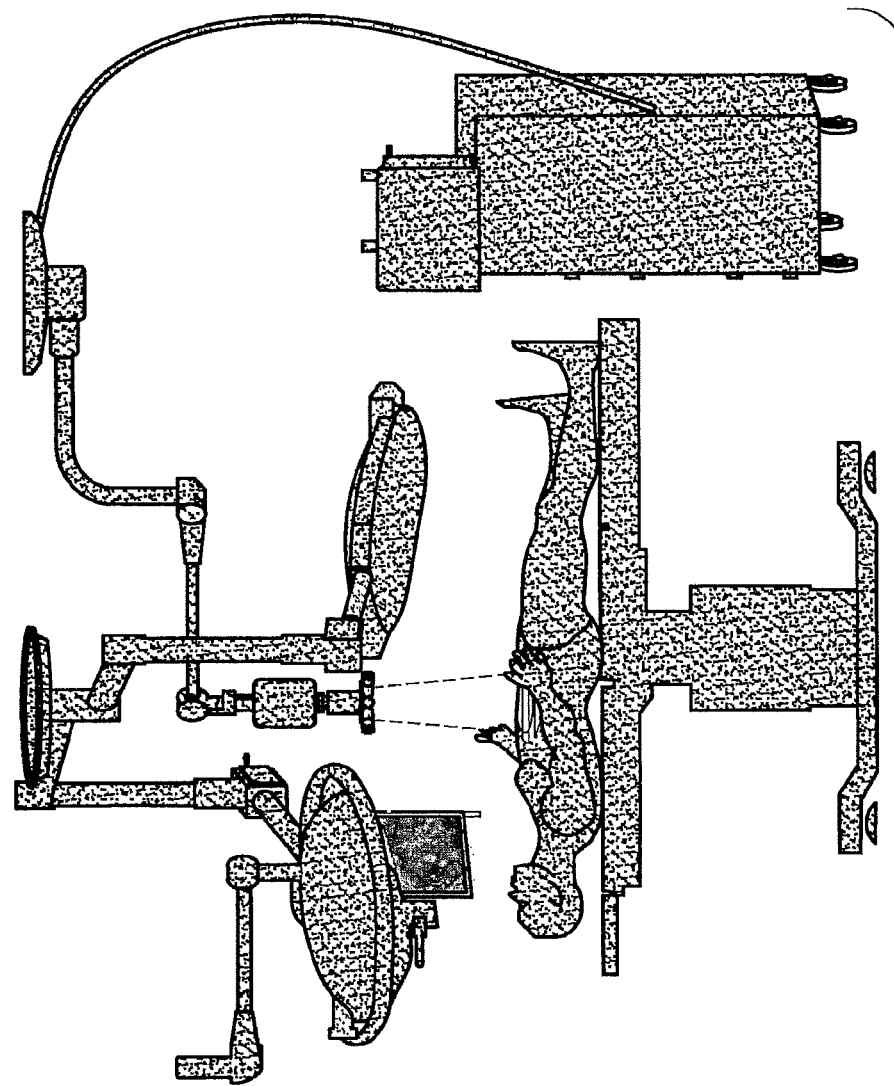
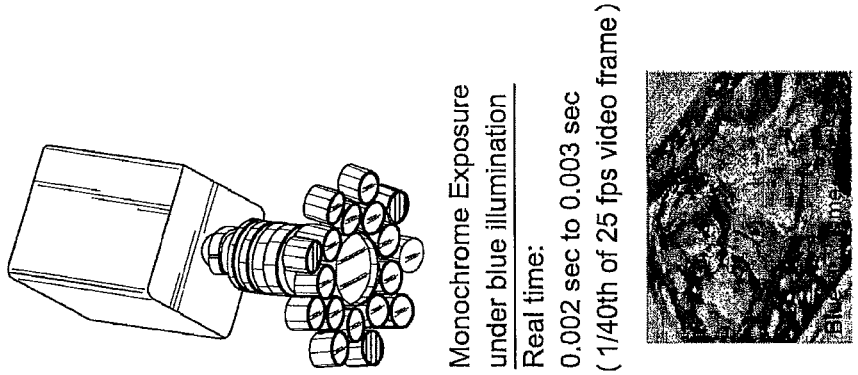
FIG. 13

Composite Video Image
(displayed at 25 frames per second)
NIR exposure is 92.5% of real
time  (RGB is remaining 7.5%)

FIG. 16

| Time → | | | | |
|---|---|---|---|---|
| Frame 0 | | | | |
| Subframe | 1 | 2 | 3 | 4 | Frame 0 Out |
| Start Time (msec) | 0 | 1 | 2 | | |
| Stop Time (msec) | 1 | 2 | 3 | | 40 |
| Lighting | Red | Green | Blue | Near-infrared | |
| Data | Red | Green | Blue | Pseudocolor | |

| Frame 1 | | | | |
|---|---|---|---|---|
| Subframe | 1 | 2 | 3 | 4 | Frame 1 Out |
| Start Time (msec) | 40 | 41 | 42 | 43 | |
| Stop Time (msec) | 41 | 42 | 43 | | 00 |
| Lighting | Red | Green | Blue | Near-infrared | |
| Data | Red | Green | Blue | Pseudocolor | |

...

| Frame n | | | | |
|---|---|---|---|---|
| Subframe | 1 | 2 | 3 | 4 | Frame n Out |
| Start Time (msec) | 40n | 40n+1 | 40n+2 | 40n+3 | |
| Stop Time (msec) | 40n+1 | 40n+2 | 40n+3 | | 40n−40 |
| Lighting | Red | Green | Blue | Near-infrared | |
| Data | Red | Green | Blue | Pseudocolor | |

FRAME-SEQUENTIAL MULTIWAVELENGTH IMAGING SYSTEM AND METHOD

CROSS REFERENCE TO RELATED APPLICATIONS

This patent application claims priority from PCT patent application PCT/US2012/057407 filed Sep. 27, 2012, which claims priority to U.S. Provisional Patent Application No. 61/540,229, filed Sep. 28, 2011, all of which are hereby incorporated by reference.

FIELD OF THE INVENTION

The present invention relates generally to imaging systems and more particularly to a frame-sequential multiwavelength imaging system and method for using the same to image a dynamic scene.

BACKGROUND OF THE INVENTION

Imaging systems that enable the display of dynamic scenes, such as an area of interest during surgery, are known. These imaging systems, however, are not proficient at detecting and displaying images that include multiple wavelengths of light, including visible light (having wavelengths from about 380 nm to about 700 nm), near-infrared light (having wavelengths from about 700 nm to about 1400 nm), and ultraviolet light (having wavelengths from about 250 nm to about 380 nm). Therefore, an improved system and method for doing so is needed.

SUMMARY OF THE INVENTION

The present invention relates to a frame-sequential multiwavelength imaging system for multiwavelength imaging of a dynamic scene. The system may comprise a wavelength switching device comprising a plurality of light sources. The light sources produce a repeated series of different wavelength profiles, each wavelength profile being sequentially applied to a dynamic scene, and the repeated series having a period of repetition. The plurality of light sources produce light with different wavelength profiles, for example at least one wavelength profile within each of a range of visible wavelength profiles and a range of near-infrared wavelength profiles. The fraction of the period of repetition that one of the different wavelength profiles, for example the at least one wavelength profile within the range of near-infrared wavelength profiles, is applied is greater than the fraction of the period of repetition that at least another of the different wavelength profiles, for example the at least one wavelength profile within the range of visible wavelength profiles, is applied. Alternatively, the wavelength switching device may comprise at least one light source which produces a repeated series of different wavelength profiles comprising at least one valid wavelength profile, when the light source is on or energized, and at least one null wavelength profile, when the light source is off or not energized, being sequentially applied to a dynamic scene, the repeated series having a period of repetition, and the at least one valid wavelength profile being applied to a dynamic scene for a fraction of the period of repetition less than the fraction of the period of repetition that the at least one null wavelength profile is applied.

The system also includes a detector that operates to detect a field of view of the dynamic scene and produce a dynamic output signal, the dynamic output signal comprising sequential frames. The sequential frames comprise image data representing the dynamic scene and correspond to the repeated series of different wavelength profiles. The sequential frames further correspond to a series of exposures of the detector to the dynamic scene, each exposure having a time interval between a start time and a stop time. The system further includes a signal processing unit, connected to the detector, for synthesizing a dynamic multiwavelength image of the dynamic scene, the dynamic multiwavelength image comprising a plurality of channels, each channel comprising image data corresponding to a different wavelength profile. The signal processing unit comprises at least one input device that receives the dynamic output signal from the detector, at least one logic device that processes the sequential frames, and at least one output device that relays the dynamic multiwavelength image to at least one of a dynamic multiwavelength image display device and a dynamic multiwavelength image recording device.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures.

FIGS. 11-15 illustrate the operation of a system to image a dynamic scene consistent with the present invention.

FIGS. 16-17 are schematic illustrations of the parameters, workflow and output of one embodiment of the system of the present invention.

DETAILED DESCRIPTION OF THE INVENTION

This application claims priority to U.S. Provisional Patent Application No. 61/540,229, filed Sep. 28, 2011, which is hereby incorporated by reference in its entirety.

Reference will now be made in detail to exemplary embodiments of the present invention, examples of which are illustrated in the accompanying drawings. Wherever possible, the same reference numbers will be used throughout the drawings to refer to the same or like parts. While the description includes exemplary embodiments, other embodiments are possible and changes may be made to the embodiments described without departing from the spirit and scope of the invention. The following detailed description does not limit the invention. Instead, the scope of the invention is defined by the appended claims and their equivalents.

Figure 1:
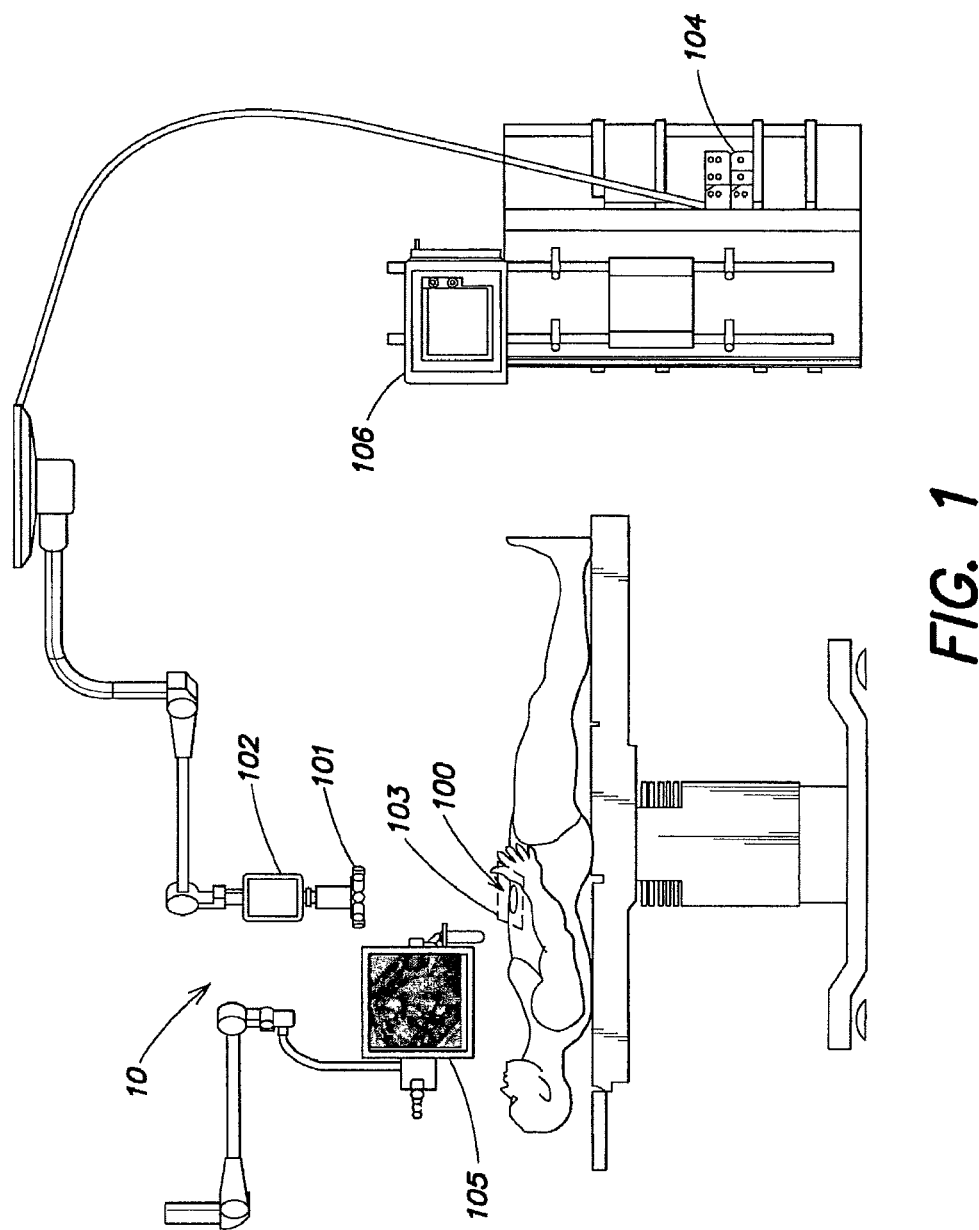
FIG. 1 shows an embodiment of the frame-sequential multiwavelength system for imaging a dynamic scene consistent with the present invention.

FIG. 1 depicts an environment 10 in which an exemplary frame-sequential multiwavelength imaging system operates. Environment 10 comprises dynamic scene 100, wavelength switching device 101, detector 102, field of view 103, signal processing unit 104, display device 105, and recording device 106.

In one embodiment, wavelength switching device 101 produces a repeated series of different wavelength profiles, with each wavelength profile being sequentially applied to a dynamic scene, such as dynamic scene 100. That is to say a first wavelength profile is applied and then substituted with the next wavelength profile and so on until the last wavelength profile is applied, and is afterwards substituted with the first wavelength profile again, and so on. The repeated series of different wavelength profiles may be capable of having a period of repetition; that is to say the time between the start of the application of the first wavelength profile and the end of the application of the last wavelength profile in the series.

Wavelength switching device 101 may comprise a plurality of light sources directed toward dynamic scene 100, with each light source producing one of the different wavelength profiles. One manner in which light from the light source may be directed toward dynamic scene 100 may involve the light sources being turned on. Alternatively or additionally, applying light to the dynamic scene 100 may involve shutters or irises being opened in front of the light sources.

Figure 3:
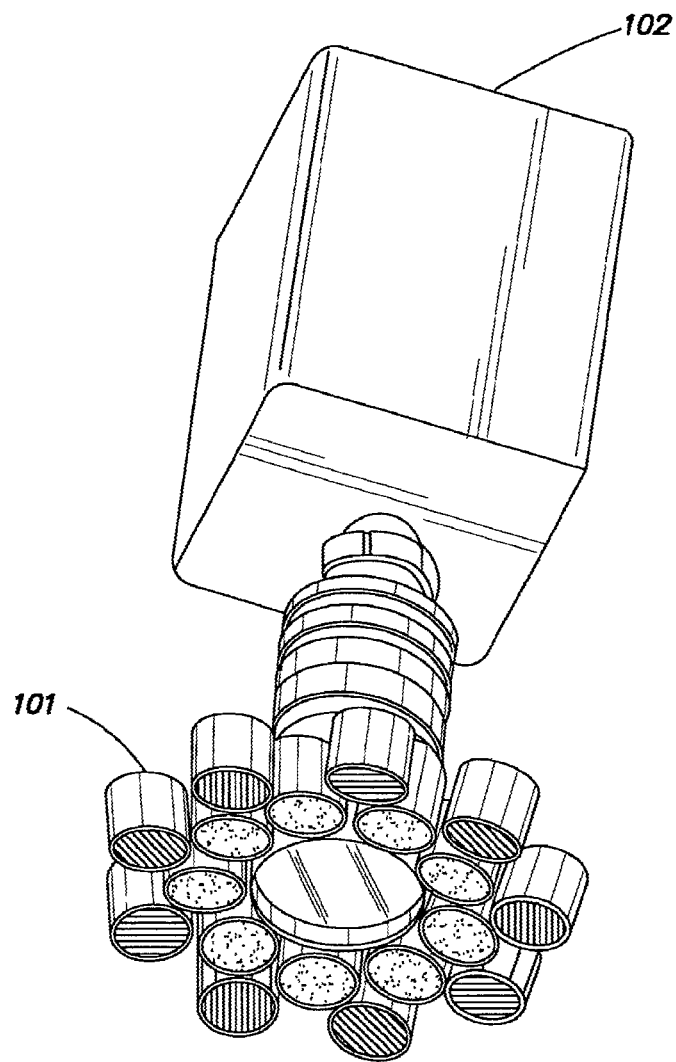
FIG. 3 shows an embodiment of the detector of the present invention in combination with the wavelength switching device.
Figure 4:
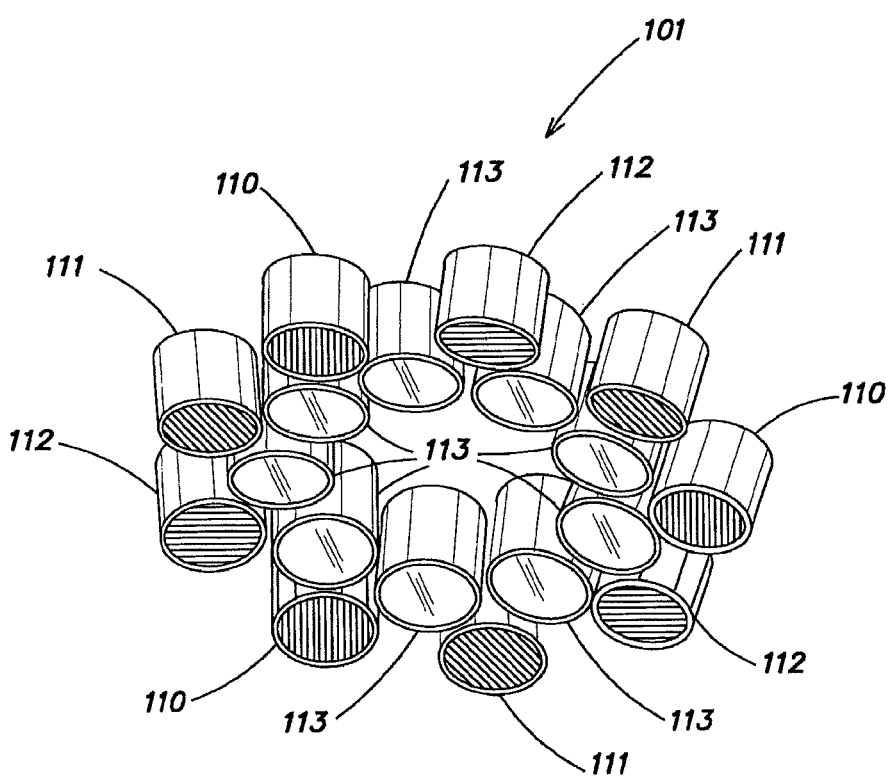
FIG. 4 shows the wavelength switching device in accordance with one embodiment of the present invention.

In one embodiment, the plurality of light sources is integral to a ring light, such as is shown in FIGS. 3 and 4. The plurality of light sources may be directed toward the dynamic scene through free space. Alternatively, the plurality of light sources can be directed toward the dynamic scene through at least one fiber optic cable.

The plurality of light sources preferably produces wavelength profiles within at least one of the ranges of wavelength profiles selected from at least one of a range of visible wavelength profiles, a range of near-infrared wavelength profiles, and a range of ultraviolet wavelength profiles and combinations thereof. In one embodiment, the plurality of light sources produce at least one wavelength profile within each of the range of visible light wavelength profiles and the range of ultraviolet wavelength profiles. In another, the plurality of light sources produce at least one wavelength profile within each of the range of visible wavelength profiles, the range of near-infrared wavelength profiles and the range of ultraviolet wavelength profiles. In still another, the plurality of light sources produce at least one wavelength profile within each of the range of visible wavelength profiles and the range of near-infrared wavelength profiles.

The wavelength profiles within the range of visible wavelength profiles may comprise at least a red wavelength profile (having wavelengths from about 620 nm to about 700 nm), a green wavelength profile (having wavelengths from about 495 nm to about 570 nm) and a blue wavelength profile (having wavelengths from about 450 nm to about 495 nm). The plurality of light sources directed toward the dynamic scene 100 can also synthesize substantially white light by persistence of vision. The substantially white light provides sufficient intensity directed toward the dynamic scene to support the useful viewing of a surgical field by the human eye.

The members of the plurality of light sources producing at least one wavelength profile within the range of visible wavelength profiles may be integral to a first ring light and the members of the plurality of light sources producing at least one wavelength profile within the range of near-infrared wavelength profiles may be integral to a second ring light. This configuration is shown in FIG. 4.

In the example of FIG. 4, light sources 110 produce a red wavelength profile, light sources 111 produce a green wavelength profile, light sources 112 produce a blue wavelength profile, and light sources 113 produce a near-infrared wavelength profile. One of skill in the art will appreciate that light sources with other wavelength profiles can be used, and that the light sources can be placed in other patterns.

Exemplary light sources may include light emitting diodes, lasers, arc lamps, fluorescent lamps, incandescent lamps, and/or other light sources known to those of ordinary skill in the art.

Detector 102 operates to detect dynamic scene 100, and a signal processing unit 104 operates to synthesize a dynamic multiwavelength image of dynamic scene 100. The dynamic multiwavelength image may comprise a plurality of channels, each channel comprising an image corresponding to a different wavelength profile. The different wavelength profiles may correspond to different reflectance images. Alternatively, the different wavelength profiles may correspond to different fluorescence images, for example, images of injected fluorescent probes or genetic reporters like fluorescent proteins. Alternatively, a null wavelength profile (e.g., when the light source is off or not energized) may correspond to a luminescence image, for example, an image of phosphorescent nanoparticles, luciferin, luminol, or any substance that glows in the dark without the need for excitation light from the light source.

Figure 2:
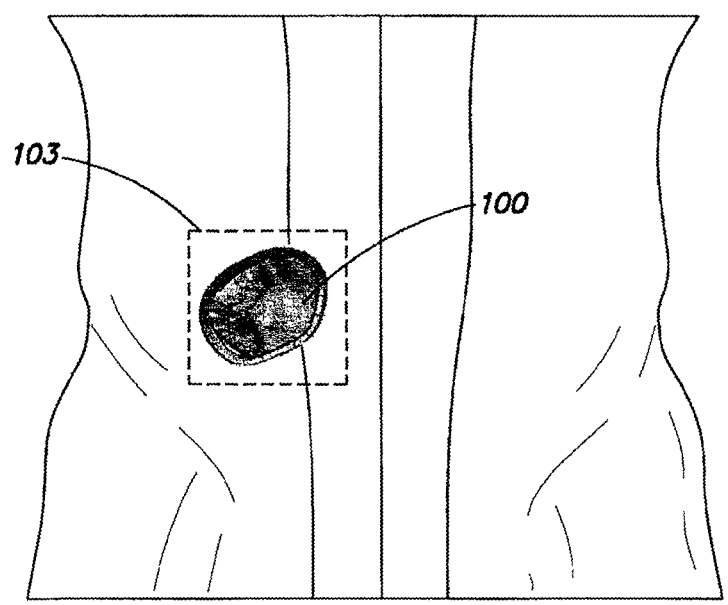
FIG. 2 shows the dynamic scene of FIG. 1 in the field of view.

In one embodiment, detector 102 detects a field of view 103 (as shown in FIGS. 1 and 2) of the dynamic scene 100 and is capable of producing a dynamic output signal. The dynamic output signal may comprise sequential frames. These sequential frames may comprise image data representing the dynamic scene 100 and correspond to the repeated series of different wavelength profiles. The sequential frames may further correspond to a series of exposures of the detector 102 to the dynamic scene 100, with each exposure having a time interval between a start time and a stop time.

The start time and the stop time of each exposure can be each synchronized with actuation of the wavelength switching device 101. In one embodiment, the start time and the stop time of each exposure can be each synchronized with a turn-on event and turn-off event, respectively, of each light source. In one embodiment, the shortest time interval of the exposure may be less than or equal to 0.1 seconds. In another embodiment, the shortest time interval of the exposure is less than or equal to 0.04 seconds. In still another embodiment, the shortest time interval of the exposure is less than or equal to 0.01 seconds. In still another embodiment, the shortest time interval of the exposure is less than or equal to 0.001 seconds. The longest time interval may, of course, be greater than 0.1 seconds. In certain embodiments, each time interval may be individually or automatically adjustable.

An exemplary detector 102 may include a camera or similar device. For example, detector 102 may include, but is not limited to: a complementary metal oxide semiconductor (CMOS) camera, a charge coupled device (CCD) camera, an electron-multiplying charge coupled device (EM-CCD), a camera for image guided surgery, a light field camera, a stereoscopic pair of cameras, an endoscope, and a laparoscope. A detector 102 may be intrinsically monochrome. Alternatively, a detector 102 may be intrinsically capable of color imaging, such as a detector comprising a sensor which comprises a color mask, for example a Bayer filter mosaic.

In one embodiment, detector 102 is capable of an intrinsic frame rate greater than the display frame rate of the dynamic multiwavelength image display device. That is to say each exposure in the series of exposures is captured in a time less than the period of repetition of the frame-sequential multiwavelength imaging system, so that the total time for capture of the entire series is less than or equal to the period of repetition of the frame-sequential multiwavelength imaging system.

Detector 102 may include a lens. One of ordinary skill in the art will appreciate that many different types of lens may be utilized. For example, the lens may be a zoom lens or a fixed lens. The lens may comprise means for automatic adjustment of zoom, focus, or f-stop, or combinations thereof. The lens may be achromatic or apochromatic. The lens may be chromatic and automatically refocused to correct for chromatic aberration synchronously with the application of the different wavelength profiles. For example, as mentioned, detector 102 may comprise a light field camera. Signal processing unit 104 may process the output signal produced by detector 102 to provide at least one of correction of chromatic aberration and extended depth-of-field imaging.

Figure 5:
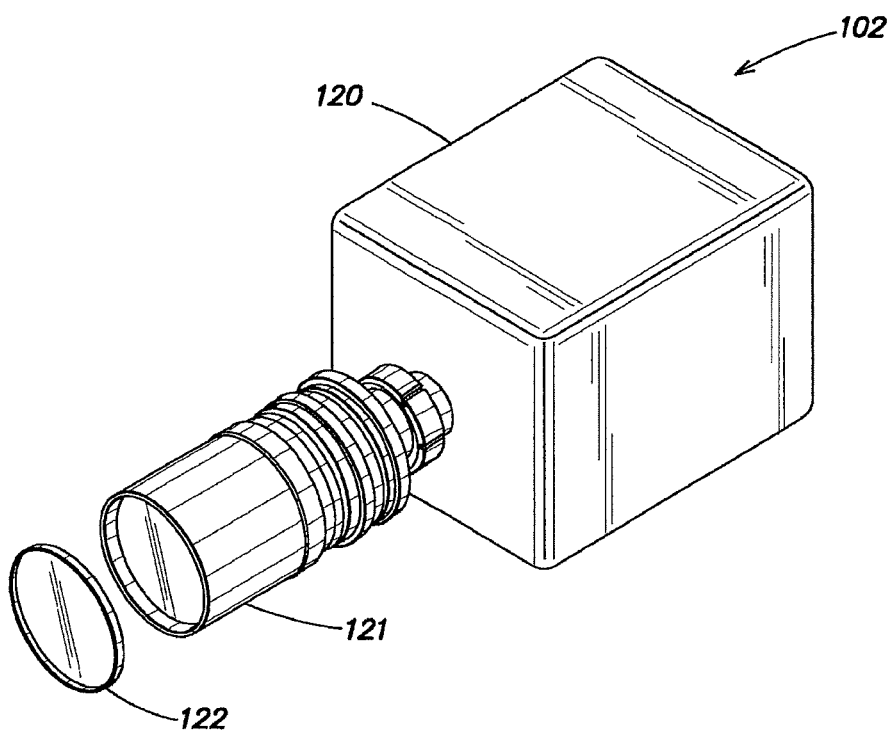
FIG. 5 shows an embodiment of the detector in accordance with the present invention.

The detector 102 may also comprise an emission filter for blocking the at least one wavelength profile within the range of near-infrared wavelength profiles and transmitting light having wavelengths longer than the at least one wavelength profile within the range of near-infrared wavelength profiles. Emission filters useful in the imaging system include those that transmit the wavelength profiles within the range of visible wavelength profiles. The emission filter may comprise an interference filter, a dichroic filter, an absorption filter, or combinations thereof. The emission filter may comprise a wide angle emission filter. FIG. 5 shows an exemplary detector 102, comprising camera 120, lens 121, and emission filter 122.

Figure 6:
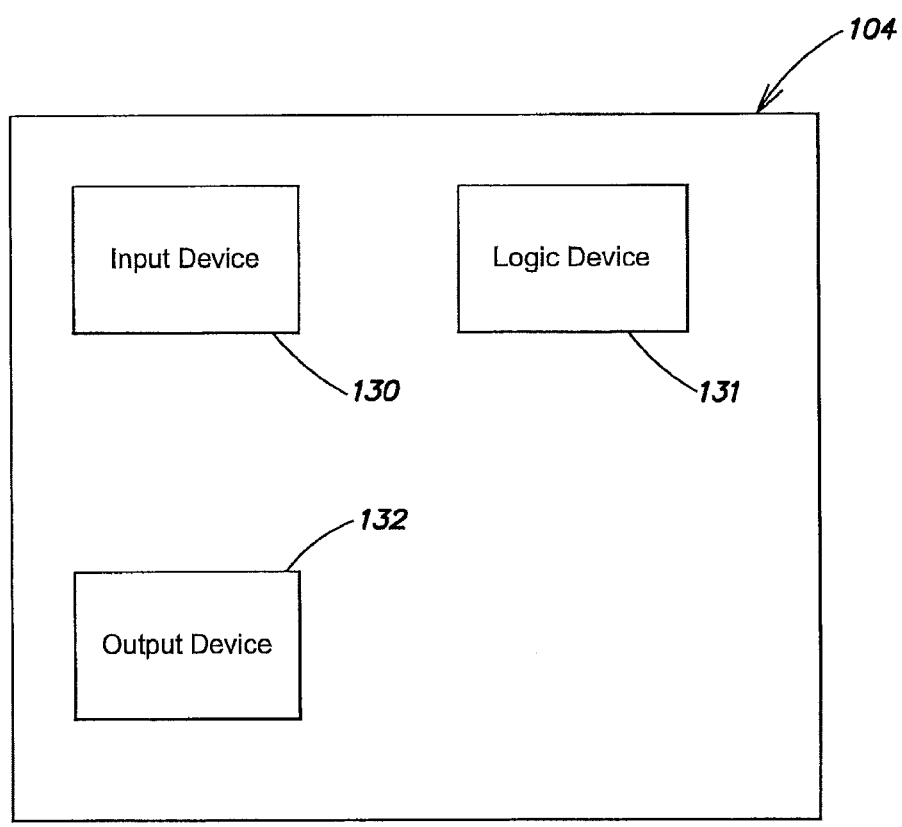
FIG. 6 shows an embodiment of the signal processing device in accordance with the present invention.

Referring to FIGS. 1 and 6, signal processing unit 104 comprises at least one input device 130, at least one logic device 131, and at least one output device 132. In one embodiment, signal processing unit 104 comprises one or more of at least one field programmable gate array (FPGA) device, at least one digital signal processing (DSP) device, at least one graphics processing unit (GPU), or at least one application specific integrated circuit (ASIC). In one embodiment, the detector 102 and the signal processing unit 104 are integral to a camera. However, one of skill in the art will appreciate that detector 102 and signal processing unit 104 need not be integral to a camera.

As mentioned, the signal processing unit 104 may comprise at least one input device 130, at least one output device 132, and at least one logic device 131. The at least one input device receives a dynamic output signal from the detector 102. The at least one logic device 131 processes sequential frames. The at least one output device 132 relays dynamic multiwavelength images. The signal processing unit 104 may connect to or is associated with at least one of a dynamic multiwavelength image display device 105 and a dynamic multiwavelength image recording device 106. The display and recording devices receive the relayed dynamic multiwavelength image from the signal processing unit 104.

The display device 105 may comprise at least one of a plurality of brightness controls and a plurality of contrast controls, which may or may not be automatic. The plurality of brightness controls and the plurality of contrast controls enable individual control of each channel and may be prompt, that is to say quickly responsive to commands. For example, upon receipt of a command the plurality of brightness controls and the plurality of contrast controls may update the image display device at the next opportunity, that is to say the next displayed frame after receipt of the command.

Figure 7:
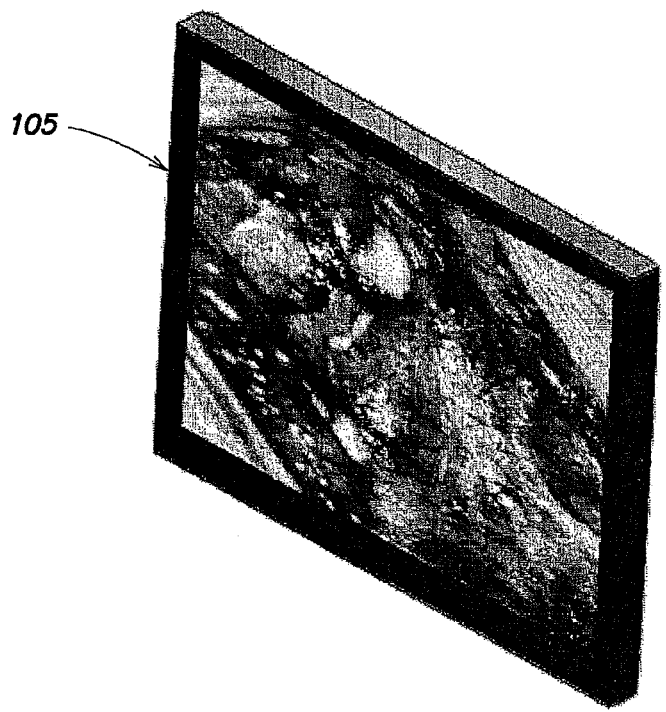
FIG. 7 shows an embodiment of the dynamic multiwavelength image display device consistent with the present invention.

The display device 105 may display the channel comprising image data corresponding to the red wavelength profile in a red display channel, the channel comprising image data corresponding to the green wavelength profile in a green display channel, the channel comprising image data corresponding to the blue wavelength profile in a blue display channel, and at least one channel comprising image data corresponding to at least one near-infrared wavelength profile in a pseudo-color display channel. The pseudo-color display channel may comprise for example a yellow color scale, a rainbow color scale, or other color scales known to those having ordinary skill in the art of rendering images. FIG. 7 shows an exemplary display device 105 that is displaying an image corresponding to dynamic scene 100. The displayed image includes image data corresponding to the red wavelength profile, green wavelength profile, blue wavelength profile, and near-infrared wavelength profile. Instead of or in addition to displaying image data on display device 105, recording device 106 may store the image data.

In addition to at least one light source directed towards dynamic scene 100, wavelength switching device 101 for use in the frame-sequential multiwavelength imaging system may also comprise at least one illumination spectral filtration system inserted in the optical path between the at least one light source and the dynamic scene. The at least one illumination spectral filtration system may produce the repeated series of different wavelength profiles.

Still further useful wavelength switching devices 101 include those comprising at least one detection spectral filtration system inserted in the optical path between the dynamic scene and the detector. In these embodiments, the at least one detection spectral filtration system produces the repeated series of different wavelength profiles.

In other embodiments, the repeated series of different wavelength profiles is capable of temporary interruption by a photographic series of wavelength profiles. The photographic series of wavelength profiles may comprise at least one of the different wavelength profiles of the repeated series.

The at least one illumination spectral filtration system may comprise at least one of the following: a rotating filter wheel, a linear variable filter, a digital micromirror device, an acousto-optic tunable filter, and a liquid crystal tunable filter.

The at least one detection spectral filtration system may comprise at least one of the following: a rotating filter wheel, a linear variable filter, a digital micromirror device, an acousto-optic tunable filter, and a liquid crystal tunable filter.

As previously mentioned, the wavelength switching device 101 may produce a repeated series of different wavelength profiles. The repeated series exhibits a period of repetition. The period of repetition may be sufficiently short so as to support useful real-time or prompt live display of a dynamic scene 100 on display device 105. In one embodiment, the period of repetition is less than or equal to about 0.1 seconds. In another embodiment, the period of repetition is less than or equal to about 0.0625 seconds. In another embodiment, the period of repetition is less than or equal to about 0.04 seconds.

In certain embodiments, the fraction of the period of repetition that the at least one wavelength profile within the range of near-infrared wavelength profiles is applied is greater than the fraction of the period of repetition that the at least one wavelength profile within the range of visible wavelength profiles is applied. Specifically, the fraction of the period of repetition that the at least one wavelength profile within the range of near-infrared wavelength profiles is applied may be 2 to 200 times greater than the fraction of the period of repetition that the at least one wavelength profile within the range of visible wavelength profiles is applied. Alternatively, the fraction of the period of repetition that the at least one wavelength profile within the range of near-infrared wavelength profiles is applied is 10 to 50 times greater than the fraction of the period of repetition that the at least one wavelength profile within the range of visible wavelength profiles is applied.

In another embodiment, the fraction of the period of repetition that the at least one wavelength profile within the range of near-infrared wavelength profiles is applied is greater than the fraction of the period of repetition that the combination of the red wavelength profile, the green wavelength profile, and the blue wavelength profile are applied. Once again, the fraction of the period of repetition that the at least one wavelength profile within the range of near-infrared wavelength profiles is applied may be 10 to 50 or 2 to 200 times greater than the fraction of the period of repetition that the combination of the red wavelength profile, the green wavelength profile, and the blue wavelength profile are applied.

One of ordinary skill in the art will recognize that other embodiments are possible wherein the one or more wavelength profiles that are applied for the greater fraction of the period of repetition are within any of the range of visible wavelength profiles, near-infrared wavelength profiles, and ultraviolet wavelength profiles; and the one or more wavelength profiles that are applied for the lesser fraction of the period of repetition are also within any of the range of visible wavelength profiles, near-infrared wavelength profiles, and ultraviolet wavelength profiles. For example, in another embodiment, the fraction of the period of repetition that a green wavelength profile is applied is greater than the fraction of the period of repetition that the combination of a yellow wavelength profile (having wavelengths from about 570 nm to about 590 nm) and a blue wavelength profile are applied. Once again, the fraction of the period of repetition that the at green wavelength profile is applied may be 10 to 50 or 2 to 200 times greater than the fraction of the period of repetition that the combination of the yellow wavelength profile and the blue wavelength profile are applied.

In another embodiment, the wavelength switching device 101 may produce a repeated series of different wavelength profiles comprising at least one valid wavelength profile (e.g., when the light source is on or energized) and at least one null wavelength profile (e.g., when the light source is off or not energized). The repeated series exhibits a period of repetition. The period of repetition may be sufficiently short so as to support useful real-time or prompt live display of a dynamic scene 100 on display device 105. In one embodiment, the period of repetition is less than or equal to about 0.1 seconds. In another embodiment, the period of repetition is less than or equal to about 0.0625 seconds. In another embodiment, the period of repetition is less than or equal to about 0.04 seconds.

In certain embodiments, the fraction of the period of repetition that the at least one valid wavelength profile is applied is less than the fraction of the period of repetition that the at least one null wavelength profile is applied. Specifically, the fraction of the period of repetition that the at least one valid wavelength profile is applied may be 2 to 200 times less than the fraction of the period of repetition that the at least one null wavelength profile is applied. Alternatively, the fraction of the period of repetition that the at least one valid wavelength profile is applied is 10 to 50 times less than the fraction of the period of repetition that the at least one null wavelength profile is applied.

In another embodiment, the fraction of the period of repetition that the at least one null wavelength profile is applied is greater than the fraction of the period of repetition that the combination of a red wavelength profile, a green wavelength profile, and a blue wavelength profile are applied. Once again, the fraction of the period of repetition that the at least one null wavelength profile is applied may be 10 to 50 or 2 to 200 times greater than the fraction of the period of repetition that the combination of the red wavelength profile, the green wavelength profile, and the blue wavelength profile are applied.

Figure 11:
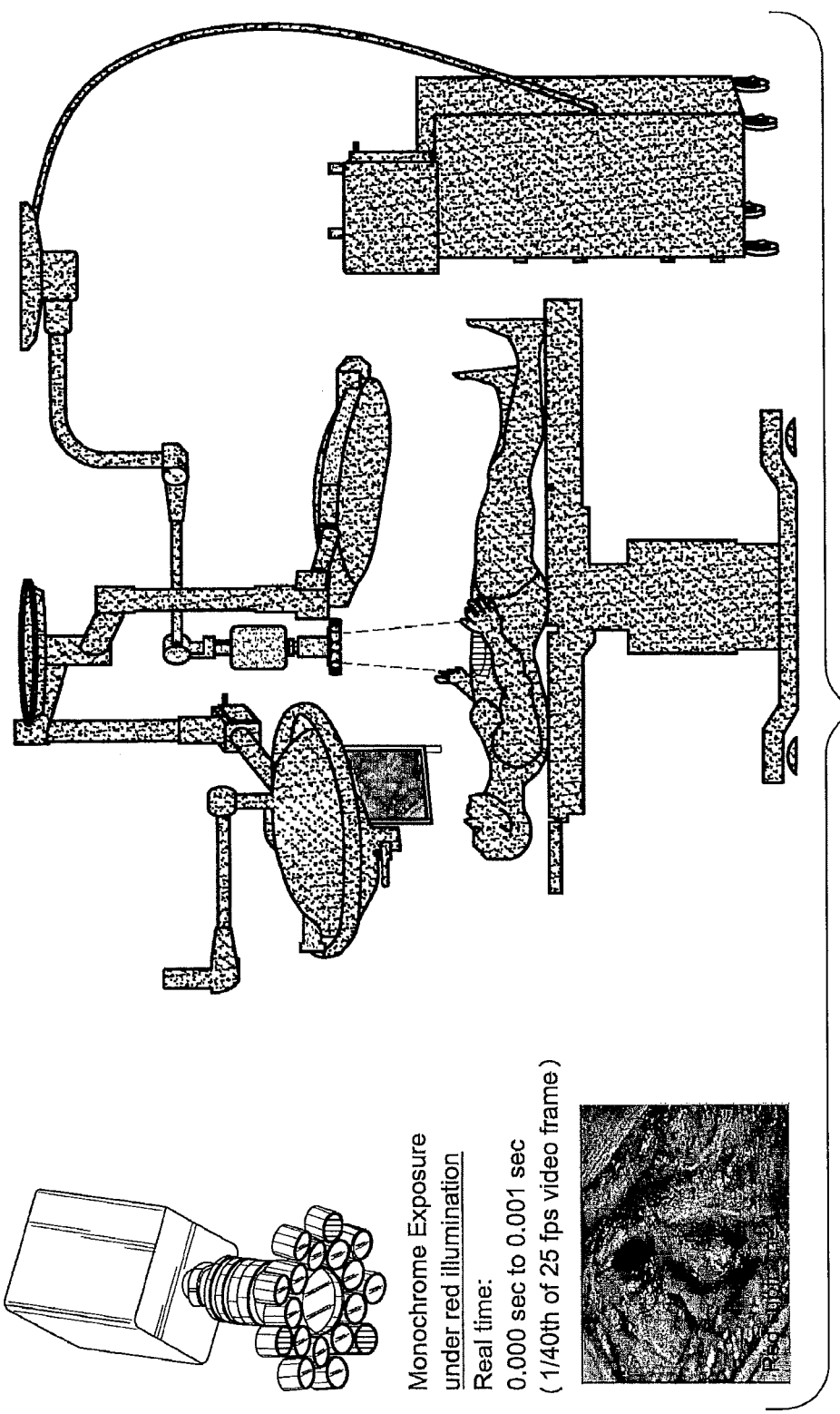
Figure 14:
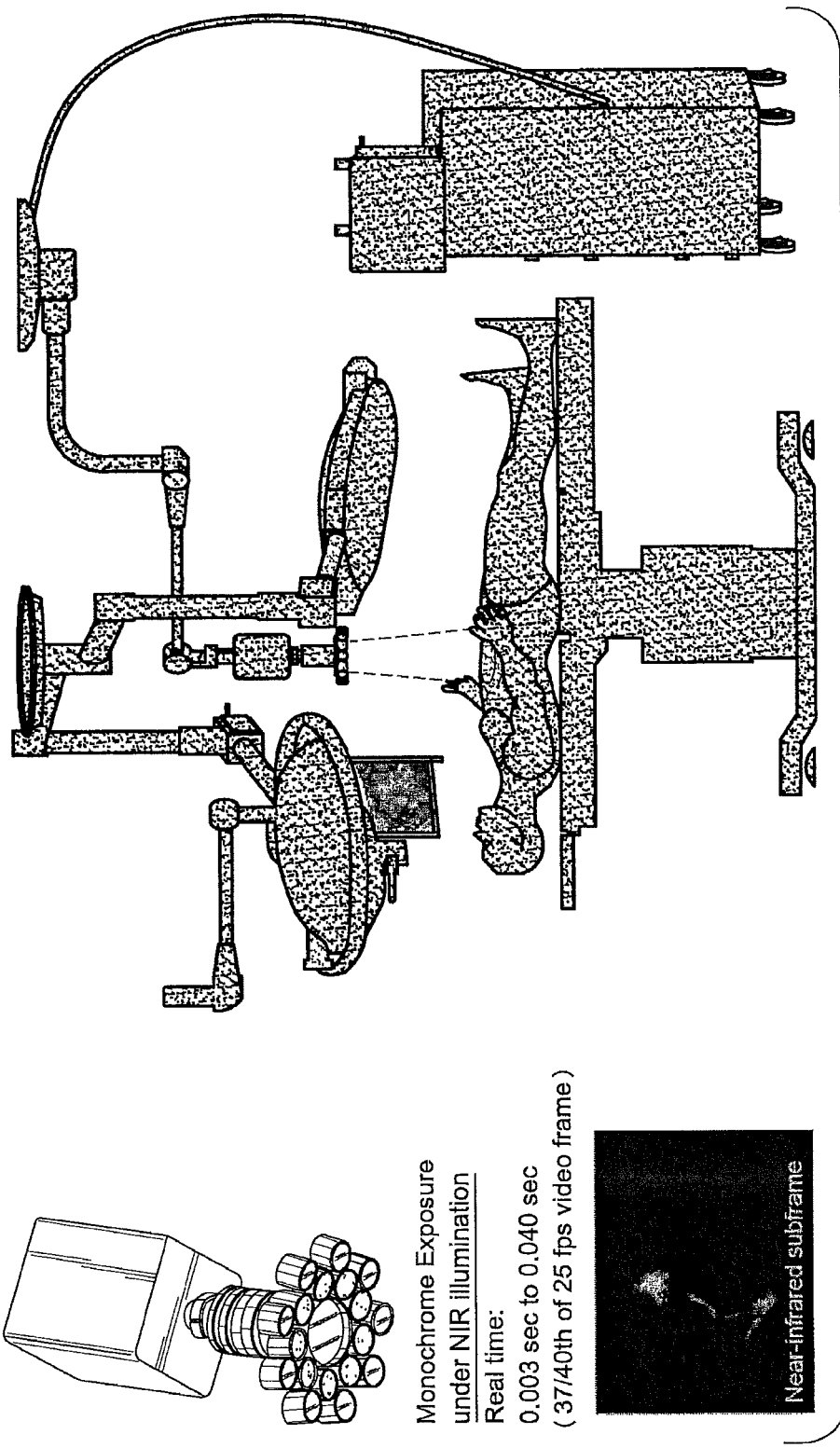

Referring to FIG. 16, in schematic form it is shown by example that each output frame is synthesized from a sequence of subframes. In this example, the detector 102 is intrinsically capable of 1000 frames per second and the output frame rate is 25 frames per second, each comprised of four subframes. Subframe 1 corresponds to a red wavelength profile of the wavelength switching device 101 and is exposed during the first millisecond of the output frame during which it collects data for the red channel. FIG. 11 depicts the operation of an exemplary imaging system during the aforementioned exemplary subframe 1. Subframe 2 corresponds to a green wavelength profile of the wavelength switching device 101 and is exposed during the second millisecond of the output frame during which it collects data for the green channel. FIG. 12 depicts the operation of an exemplary imaging system during the aforementioned exemplary subframe 2. Subframe 3 corresponds to a blue wavelength profile of the wavelength switching device 101 and is exposed during the third millisecond of the output frame during which it collects data for the blue channel. FIG. 13 depicts the operation of an exemplary imaging system during the aforementioned exemplary subframe 3. Subframe 4 corresponds to a near-infrared wavelength profile of the wavelength switching device 101 and is exposed during the remaining 37 milliseconds of the output frame during which it collects data for the pseudo-color channel. FIG. 14 depicts the operation of an exemplary imaging system during the aforementioned exemplary subframe 4.

The emission filter may block the near-infrared wavelength profile of the near-infrared light source and transmit light having wavelengths longer than the near-infrared wavelength profile of the near-infrared light source and also light having wavelengths corresponding to the red, green and blue wavelength profiles, so that the data collected for the pseudo-color channel comprises fluorescence image data. This sequence of subframes may be repeated to produce a dynamic multiwavelength image.

Figure 8:
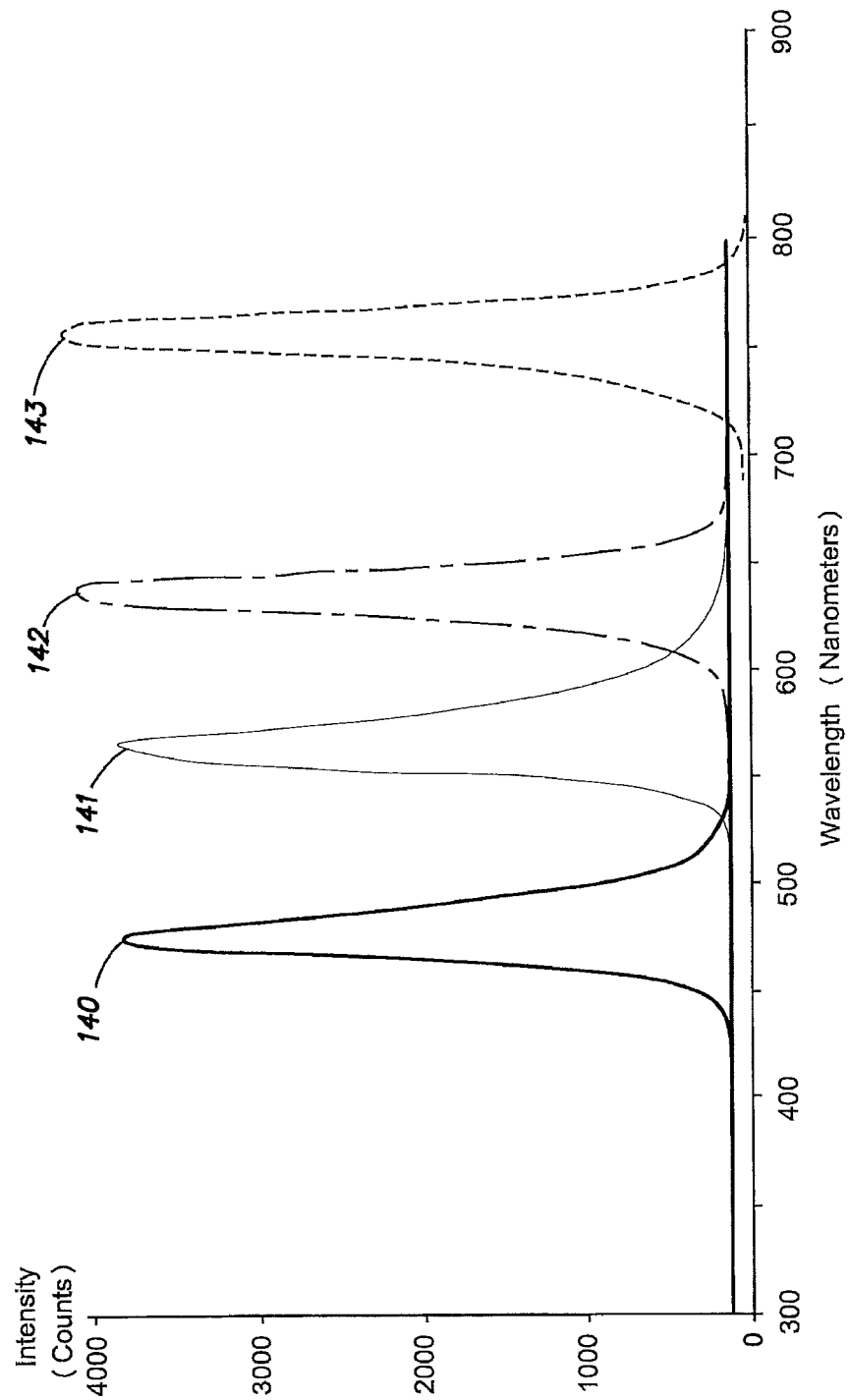
FIG. 8 shows exemplary wavelength profiles consistent with the present invention.
Figure 9:
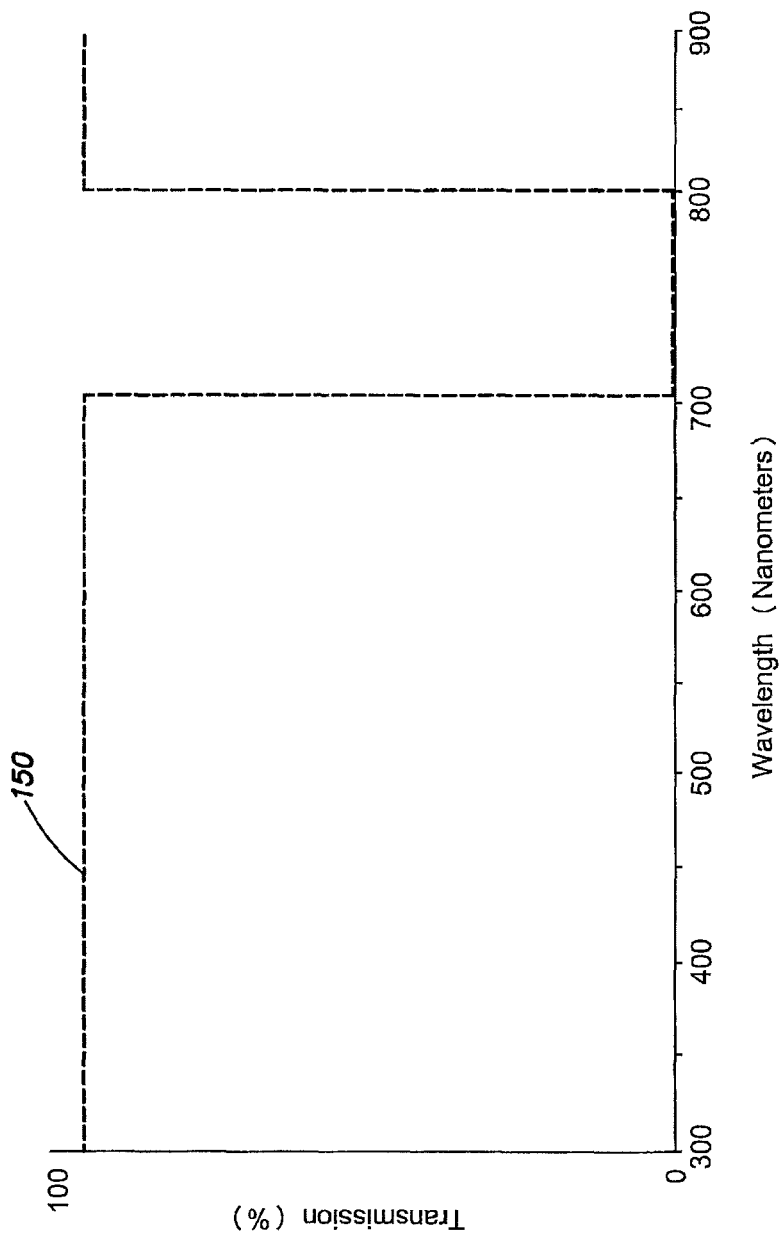
FIG. 9 shows a filter transmission spectrum consistent with the present invention.
Figure 10:
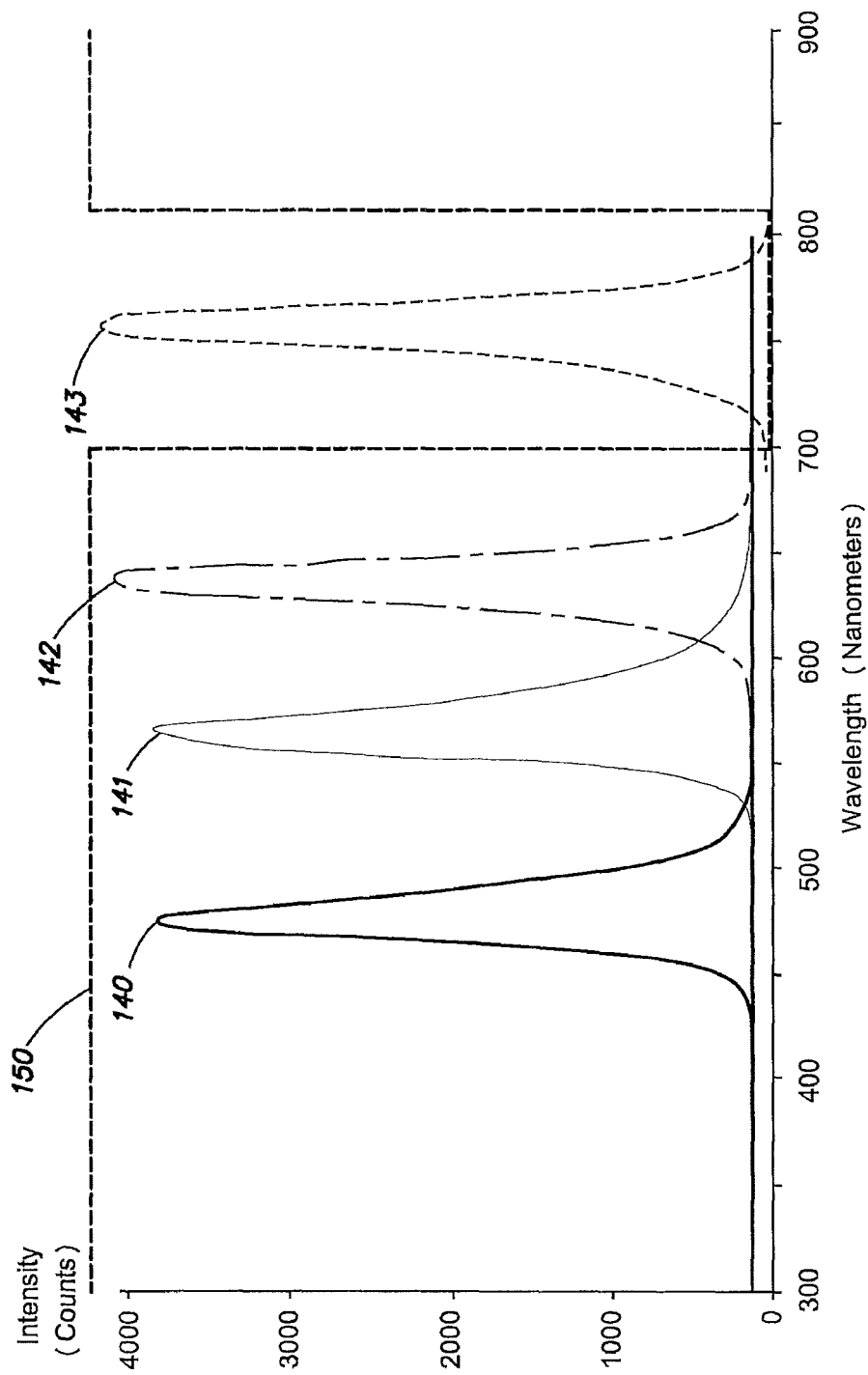
FIG. 10 is an overlay of FIG. 8 and FIG. 9.

FIGS. 8-10 demonstrate the aforementioned emission filter operation. Blue wavelength profile 140, green wavelength profile 141, and red wavelength profile 142 are transmitted, while near-infrared wavelength profile 143 is blocked (as indicated by filter transmission curve 150), so that data collected for the pseudo-color channel comprises fluorescence image data.

Figure 15:
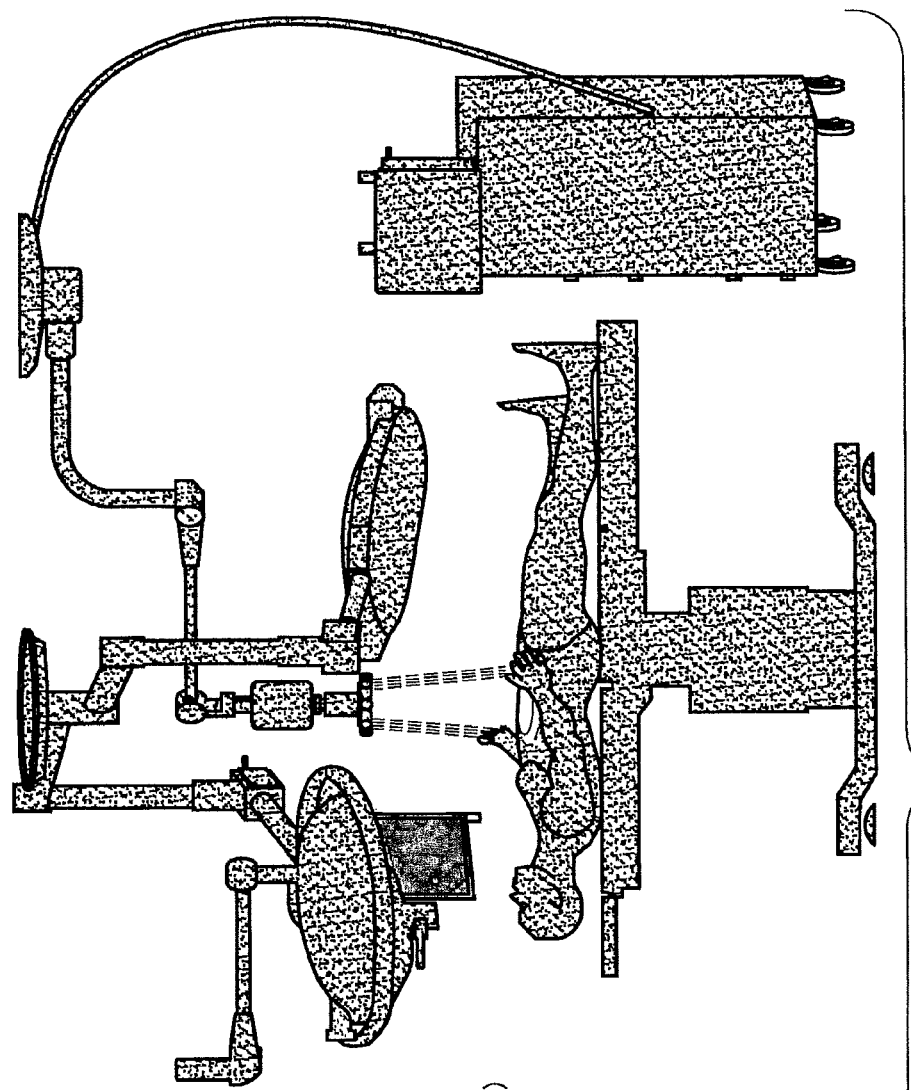

The signal processing unit 104 in this example delivers an output signal to at least one of the dynamic multiwavelength image display device 105 and dynamic multiwavelength image recording device 106 which overlays the pseudo-color channel onto the full color composite of the red, green, and blue channels, wherein the dynamic multiwavelength image is updated at 25 frames per second. FIG. 15 depicts an exemplary imaging system where the display device has overlayed the pseudo-color channel onto the full color composite of the red, green, and blue channels.

Figure 17:
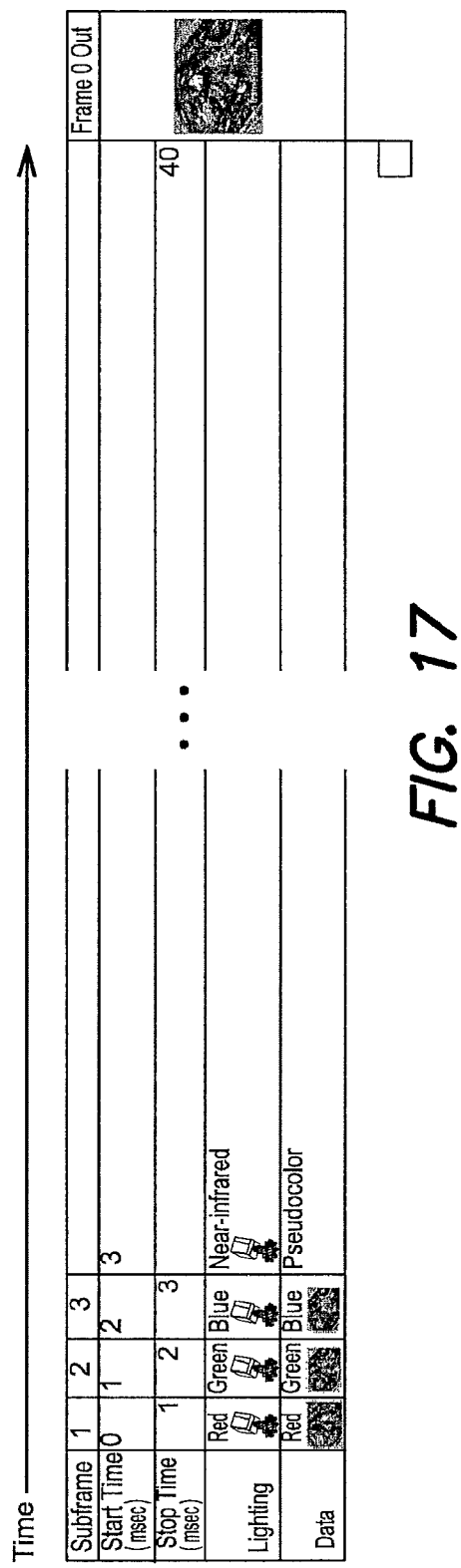

Referring to FIG. 17, in schematic form it is shown by example that subframe 4 can be temporarily modified, for example on demand, to a longer exposure time, for example 0.997 seconds, which is particularly useful for a slow update or photographic pause mode of the frame-sequential multiwavelength imaging system.

The display device 105 may update the pseudo-color display channel at a slower rate than it updates the red, green and blue display channels. In another example, the detector 102 is intrinsically capable of 1000 frames per second and outputs two distinct frame streams. The first output frame stream rate is 25 frames per second, wherein each frame in the stream is comprised of three subframes, namely subframes 1, 2, and 3. Subframe 1 corresponds to a red wavelength profile of the wavelength switching device and is exposed during the first millisecond of the output frame during which it collects data for the red channel. Subframe 2 corresponds to a green wavelength profile of the wavelength switching device and is exposed during the second millisecond of the output frame during which it collects data for the green channel. Subframe 3 corresponds to a blue wavelength profile of the wavelength switching device and is exposed during the third millisecond of the output frame during which it collects data for the blue channel. The second output frame stream rate is 12.5 frames per second, wherein each frame in the stream is comprised of two subframes, namely subframes 4 and 5. Subframes 4 and 5 correspond to a near-infrared wavelength profile of the wavelength switching device. Subframe 4 is exposed during the remaining 37 milliseconds (while the red, green, and blue wavelength profiles are not being applied) of a first frame of the first output frame stream, during which it collects a first subset of data for the pseudo-color channel. Subframe 5 is exposed during the remaining 37 milliseconds (while the red, green, and blue wavelength profiles are not being applied) of a consecutive second frame of the first output frame stream, during which it collects a second subset of data for the pseudo-color channel. The first and second subsets of data for the pseudo-color channel are added or averaged together by the signal processing unit. This sequence of subframes may be repeated to produce a dynamic multiwavelength image. The signal processing unit in this example delivers an output signal to at least one of the dynamic multiwavelength image display device 105 and dynamic multiwavelength image recording device 106 which overlays the pseudo-color channel, updated at 12.5 frames per second, onto the full color composite of the red, green and blue channels, updated at 25 frames per second.

Figure 18:
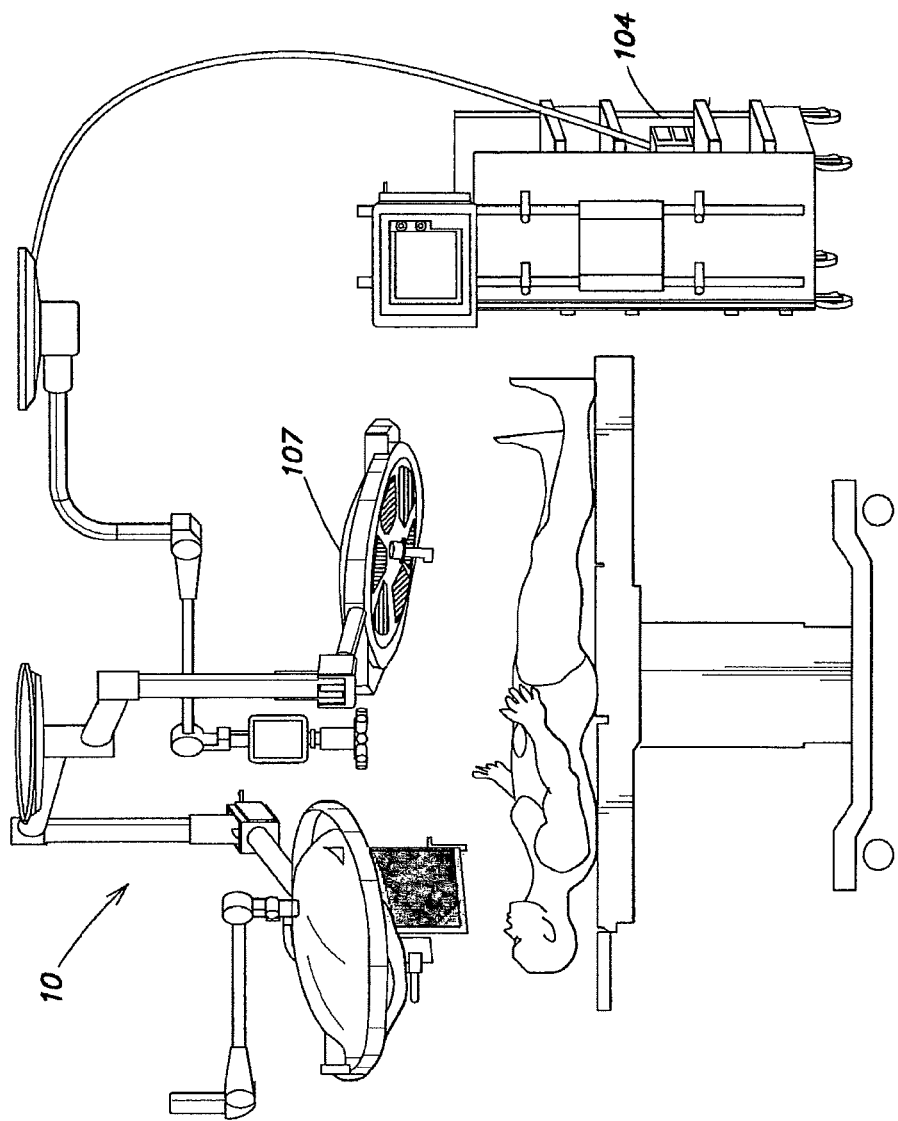
FIG. 18 shows one embodiment of the frame-sequential multiwavelength system of the present invention in use in a surgical setting.
Figure 19:
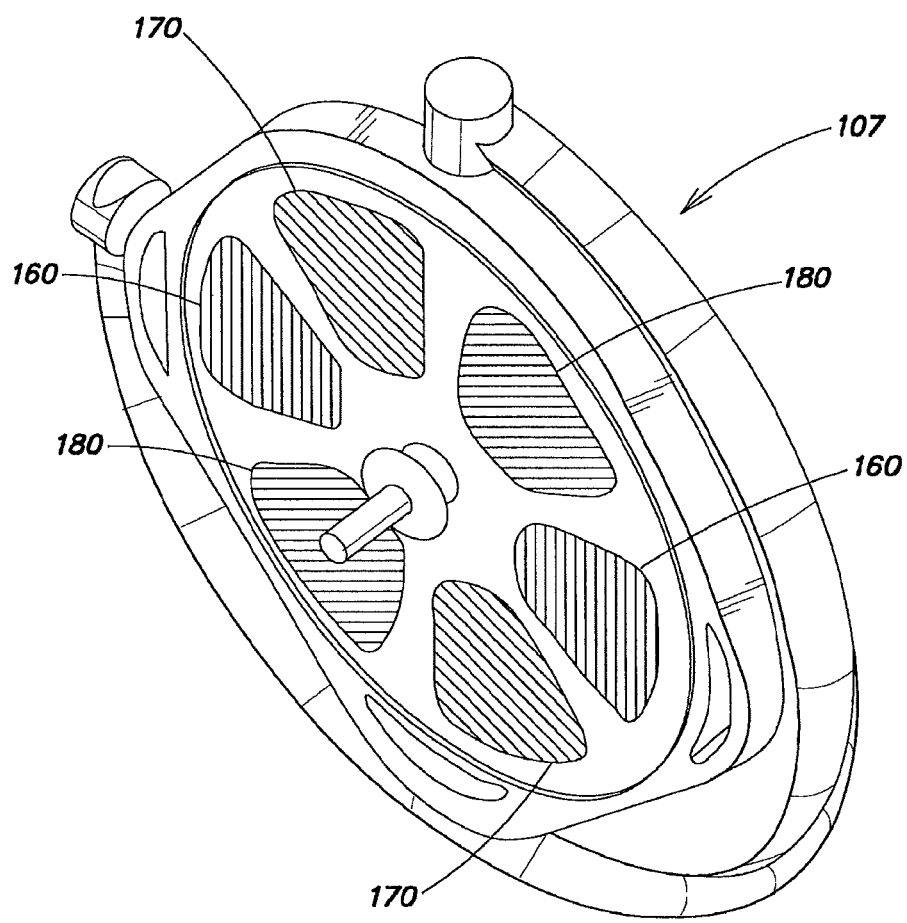
FIG. 19 shows one embodiment of the auxiliary light source of the present invention.
Figure 20:
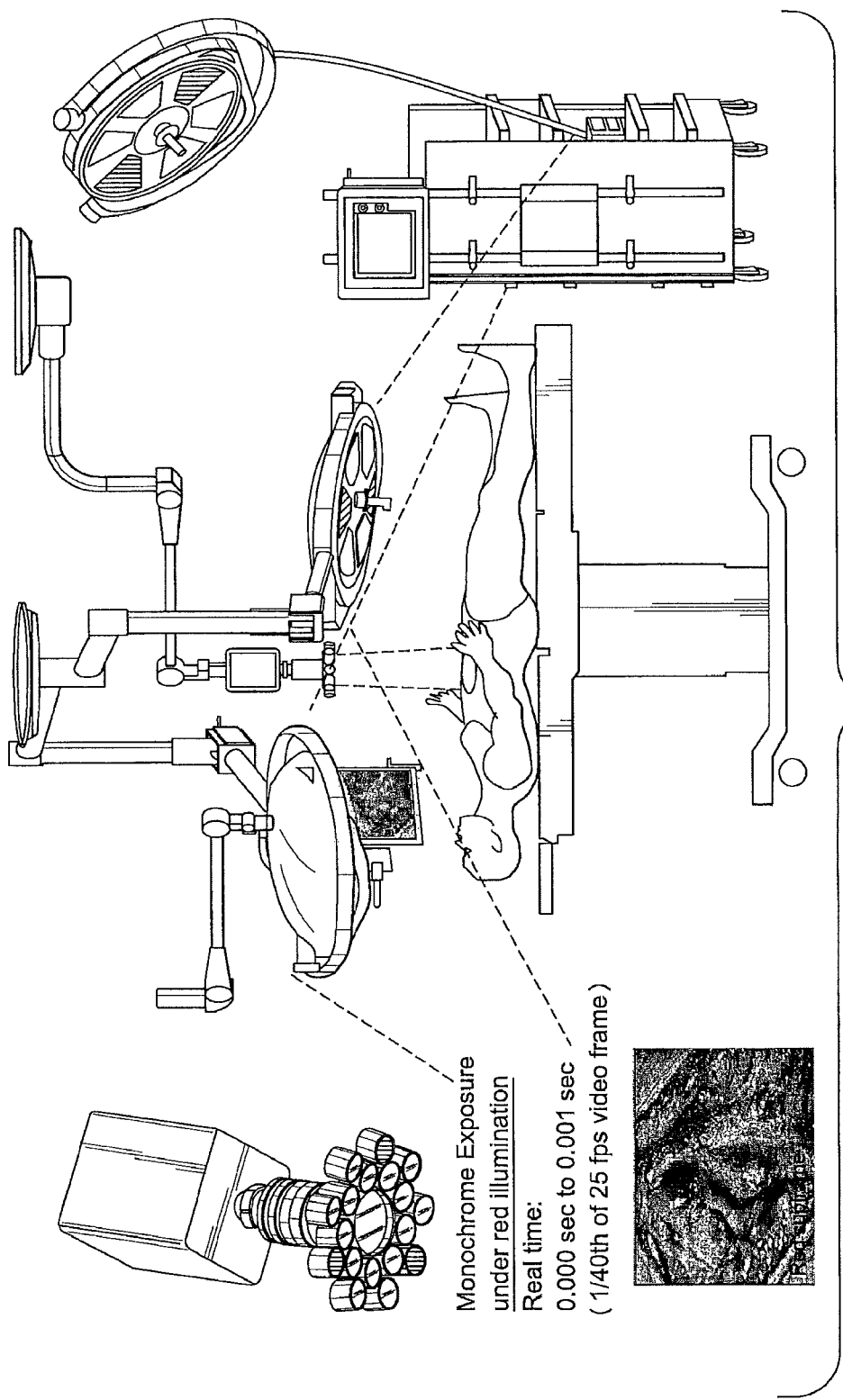
FIGS. 20-24 show embodiments of the frame-sequential multiwavelength imaging system of the present invention in use in a surgical setting.
Figure 21:
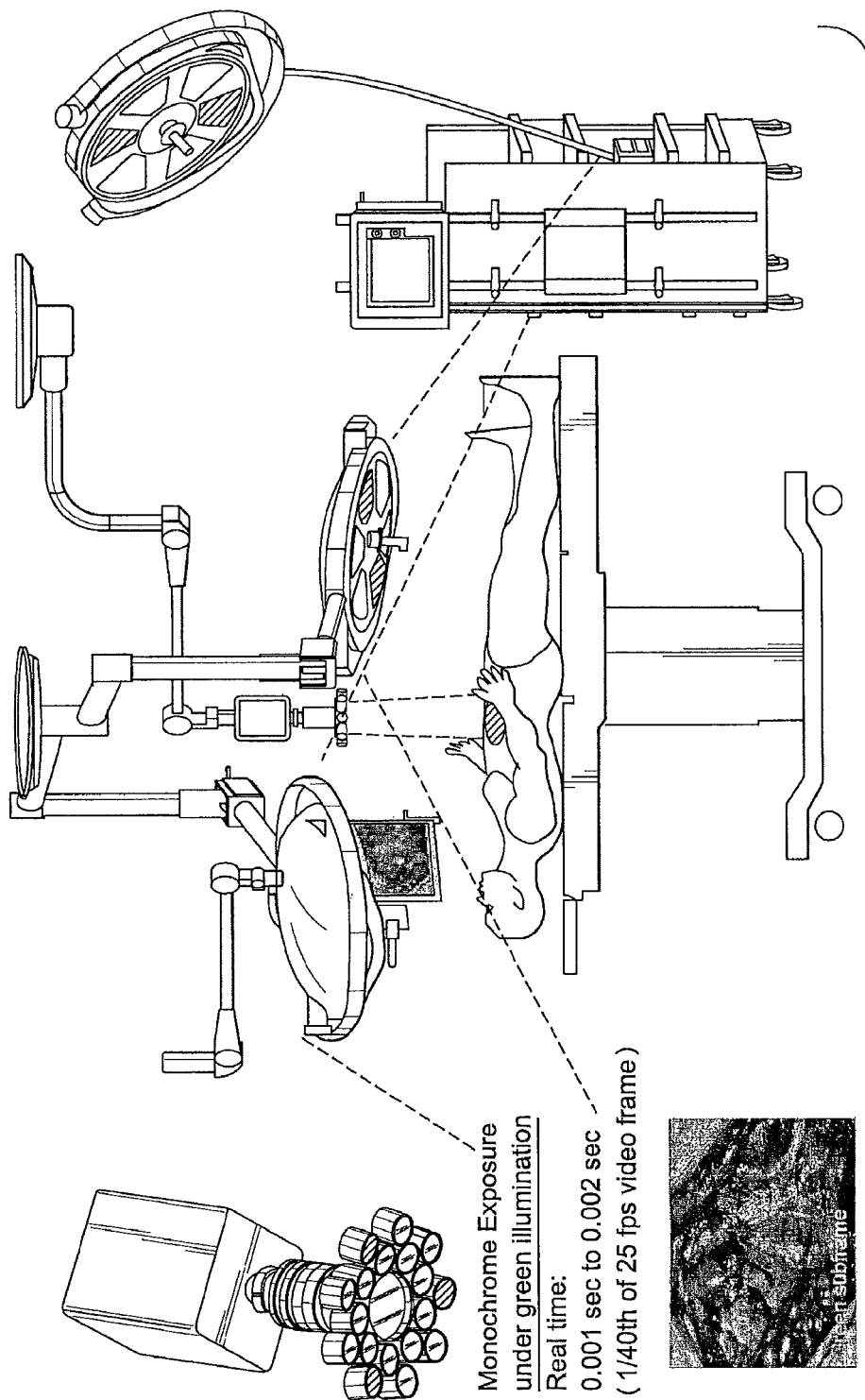
Figure 22:
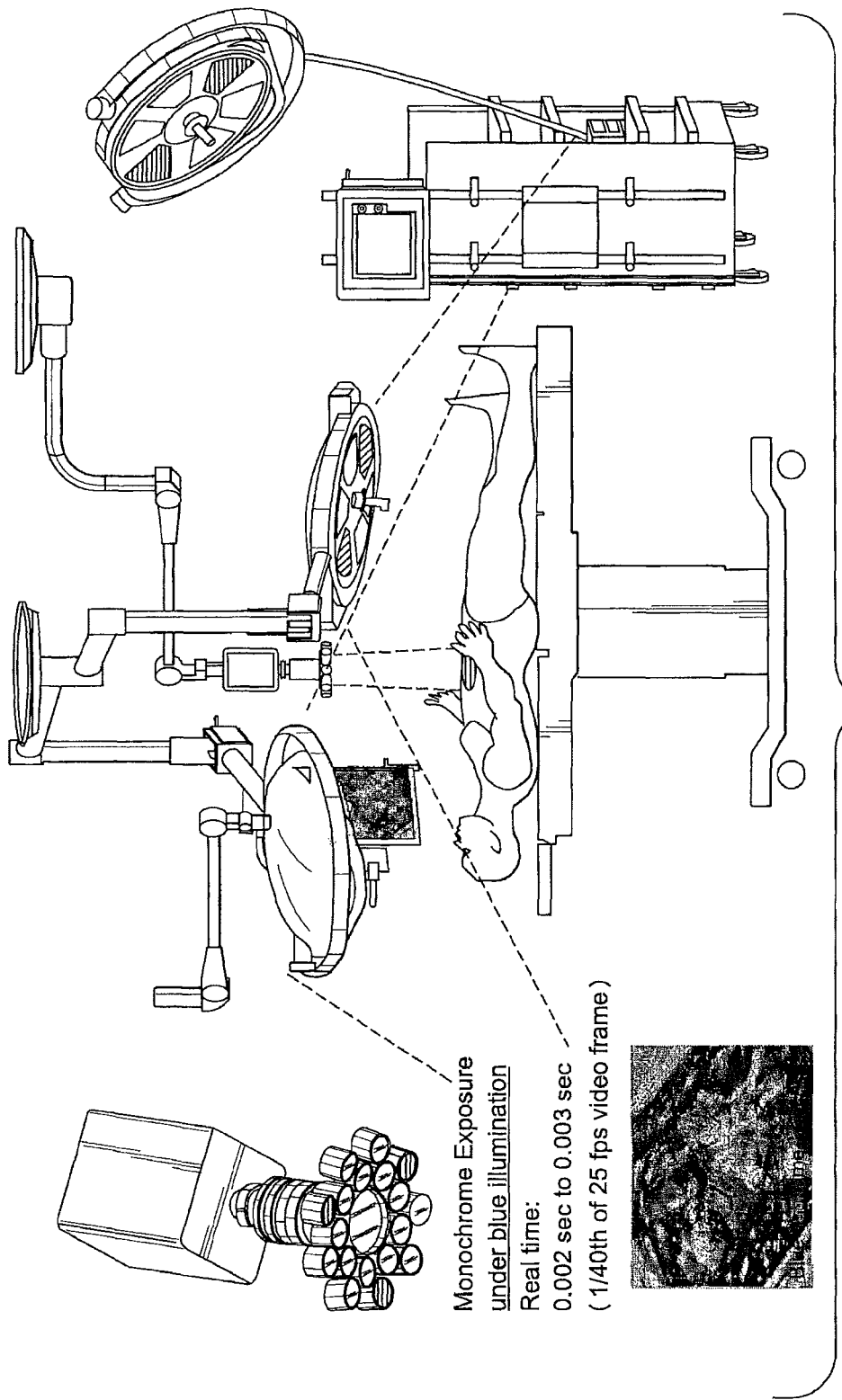
Figure 23:
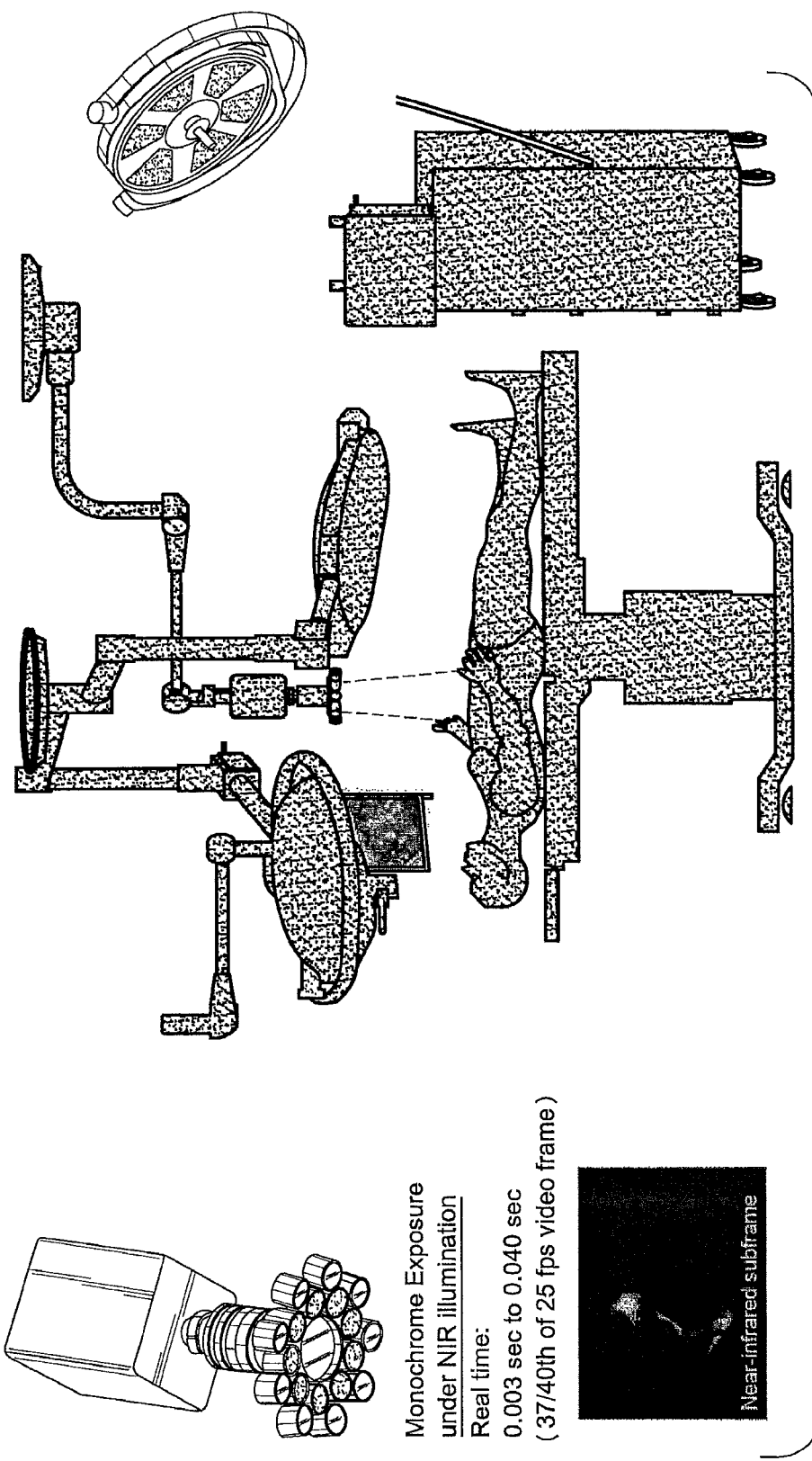

Referring to FIGS. 18 and 19, in one embodiment, the frame-sequential multiwavelength imaging system may further comprise at least one auxiliary light source 107 positioned for ambient lighting in an environment beyond the field of view of the detector. The at least one auxiliary light source 107 may produce one of the different wavelength profiles synchronously with the wavelength switching device 101, by means of a synchronization device, during the time that the wavelength switching device 101 produces substantially the same one of the different wavelength profiles. The synchronization device may comprise a wireless communication device, a wired communication device, or other communication device.

A plurality of light sources may be present in an auxiliary light source 107. In one embodiment, the plurality of light sources of auxiliary light source 107 may comprise at least first, second, and third light sources positioned for ambient lighting in an environment beyond the field of view of the detector 102. The first light source 160 substantially produces the red wavelength profile synchronously, by means of the synchronization device, during the time that the wavelength switching device 101, for example at least one of the light sources directed toward the dynamic scene, produces the red wavelength profile. The second light source 170 substantially produces the green wavelength profile synchronously, by means of the synchronization device, during the time that the wavelength switching device, for example at least one of the light sources directed toward the dynamic scene, produces the green wavelength profile. And the third light source 180 substantially produces the blue wavelength profile synchronously, by means of the synchronization device, during the time that the wavelength switching device, for example at least one of the light sources directed toward the dynamic scene, produces the blue wavelength profile.

An auxiliary light source 107 may also include at least one auxiliary illumination spectral filtration system inserted in the optical path between the at least one light source and human observers of the auxiliary light source. The at least one auxiliary illumination spectral filtration system may substantially produce the repeated series of different wavelength profiles.

Exemplary auxiliary light sources may include light emitting diodes, lasers, arc lamps, fluorescent lamps, incandescent lamps, and other light sources known to those of ordinary skill in the art.

The at least one auxiliary illumination spectral filtration system may comprise at least one of the following: a rotating filter wheel, a linear variable filter, a digital micromirror device, an acousto-optic tunable filter, and a liquid crystal tunable filter.

The at least one auxiliary light source or plurality of auxiliary light sources may comprise one or more of at least one overhead lighting device and at least one surgical headlamp device. The plurality of auxiliary light sources may synthesize substantially white light by persistence of vision. The substantially white light may provide sufficient ambient intensity useful for human vision in a surgical operating room.

Figure 24:
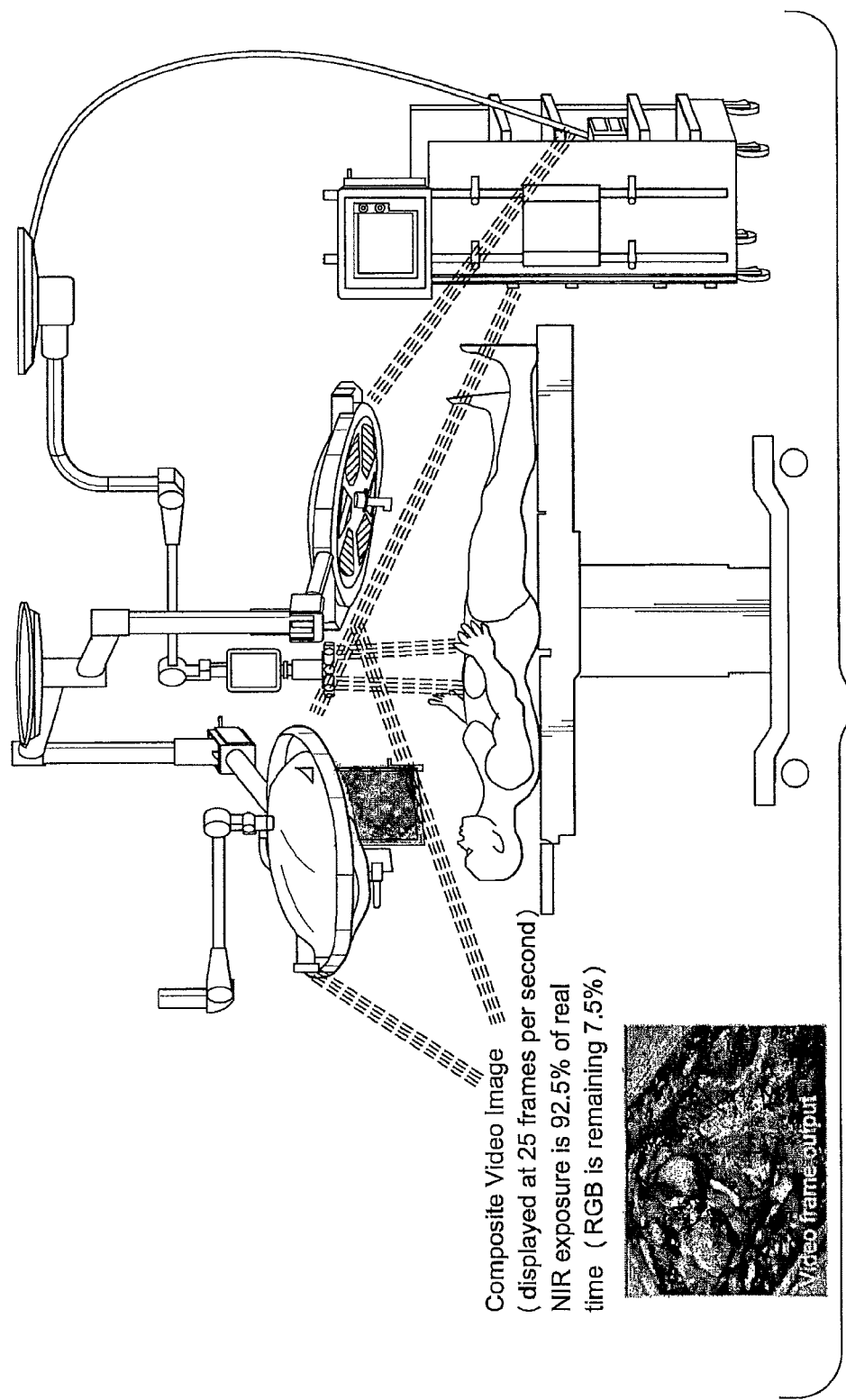

FIGS. 20-23, like FIGS. 11-14, respectively, show the operation of an exemplary imaging system during exemplary subframes corresponding to red, green, blue, and near-infrared wavelength profiles. However, in addition to the light from wavelength switching device 101, FIGS. 20-23 also show that light emanates from one or more auxiliary light sources, such as auxiliary light source 107. FIG. 24, like FIG. 15, depicts an exemplary imaging system where the display device has overlayed the pseudo-color channel onto the full color composite of the red, green, and blue channels.

Figure 25:
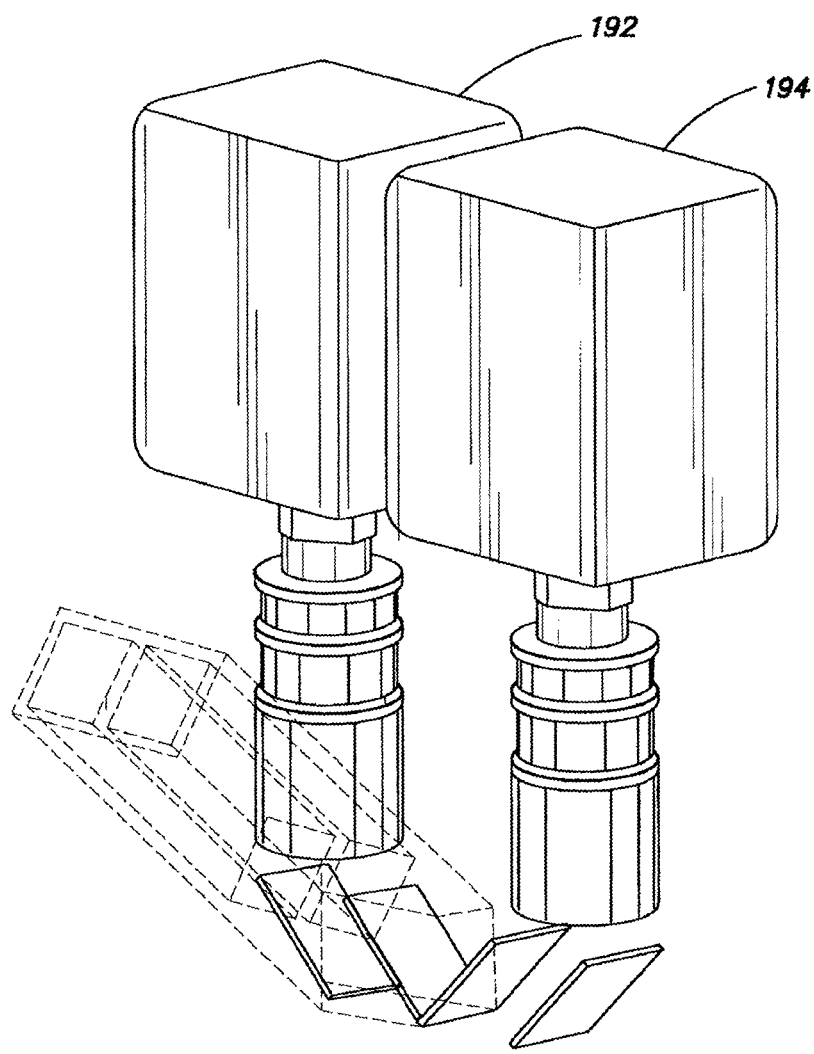
FIG. 25 shows an embodiment of the frame-sequential multiwavelength system in a stereoscopic 3D configuration.

FIG. 25 shows an embodiment of the frame-sequential multiwavelength system in a stereoscopic 3D configuration. In this embodiment, two detectors (192, 194) are configured in an optical system such that the imaging paths of the detectors are separated in space, for example to simulate the separation of the eyes of a human individual as necessary for binocular vision affording depth perception. Each of detectors 192 and 194 may operate in a manner similar to detector 102. As shown in FIG. 25, the separation in space may be achieved by a dual periscope assembly comprised of mirrors. The stereoscopic 3D configuration also includes a viewer which comprises two small screens, each screen providing a dynamic multiwavelength image, as described previously, to each of the eyes of the human viewer, wherein each dynamic multiwavelength image corresponds to each of the detectors. Alternative stereoscopic 3D configurations may include a head mounted display.

Figure 26:
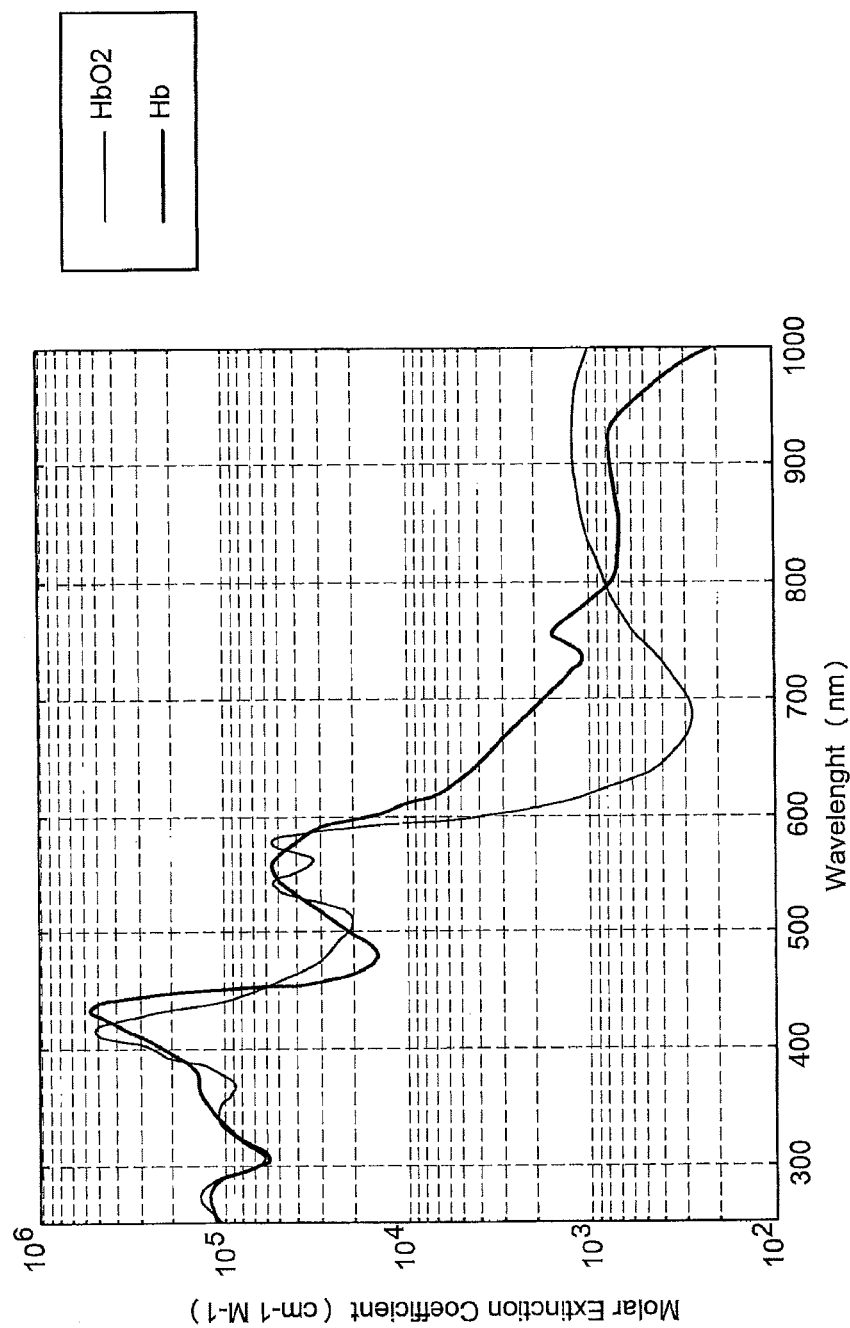
FIG. 26 shows the known molar extinction coefficients of $HbO_2$ and $Hb$.

Referring to FIG. 26 as related to an application of the frame-sequential multiwavelength imaging system for oxy-/deoxyhemoglobin imaging: the absorption coefficient ($\mu_a$) is defined as the probability of photon absorption in tissue per unit path length. Different tissue components have different $\mu_a$ values. Moreover, $\mu_a$ is a function of wavelength. Blood consists of two different types of hemoglobin: oxyhemoglobin ($HbO_2$) is bound to oxygen, while deoxyhemoglobin (Hb) is unbound to oxygen. These two different types of hemoglobin exhibit different absorption and reflectance spectra that are normally represented in terms of molar extinction coefficients, as shown in FIG. 26. The molar extinction coefficient of Hb has its highest absorption peak at 420 nm and a second peak at 580 nm. Its spectrum then gradually decreases as light wavelength increases. On the other hand, $HbO_2$ shows its highest absorption peak at 410 nm, and two secondary peaks at 550 nm and 600 nm. As light wavelengths increase beyond 600 nm, $HbO_2$ absorption decays much faster than Hb absorption. The points where the molar extinction coefficient spectra of Hb and $HbO_2$ intersect are called isosbestic points.

By using two different wavelengths, it is possible to calculate the concentrations of oxyhemoglobin ($C_{HbO2}$) and deoxyhemoglobin ($C_{Hb}$) as shown in the following equations:

$$\mu_a(\lambda_1)=\ln(10)\epsilon_{HbO2}(\lambda_1)C_{HbO2}+\ln(10)\epsilon_{Hb}(\lambda_1)C_{Hb} \quad \text{Equation 1:}$$

$$\mu_a(\lambda_2)=\ln(10)\epsilon_{HbO2}(\lambda_2)C_{HbO2}+\ln(10)\epsilon_{Hb}(\lambda_2)C_{Hb} \quad \text{Equation 2:}$$

Here, $\lambda_1$ and $\lambda_2$ are the two wavelengths; $\epsilon_{HbO2}$ and $\epsilon_{Hb}$ are the molar extinction coefficients of $HbO_2$ and Hb, respectively; $C_{HbO2}$ and $C_{Hb}$ are the molar concentrations of $HbO_2$ and Hb in tissue, respectively. Oxygen saturation ($SO_2$) can then be computed as:

$$SO_2 = \frac{C_{HbO2}}{C_{HbO2} + C_{Hb}} \quad \text{Equation 3}$$

The computation of oxygen saturation may be achieved on a pixel-by-pixel basis in a dynamic multiwavelength image produced by the frame-sequential multiwavelength imaging system by configuring the wavelength switching device to apply $\lambda_1$ and $\lambda_2$ and configuring the signal processor to perform the calculation of equation 3 on a pixel-by-pixel basis. The numerical results of the calculation may be mapped to a pseudo-color scale, as previously mentioned, and displayed on the dynamic multiwavelength imaging device 105 or recorded by the dynamic multiwavelength recording device 106 or both. Furthermore, the pseudo-color image of oxygen saturation may be overlayed onto a dynamic anatomical image comprised of at least one channel corresponding to a wavelength profile representative of the plain reflectance of the dynamic scene. Additionally, the pseudo-color image of oxygen saturation may be overlayed onto a dynamic anatomical image comprised of red, green, and blue channels corresponding to red, green, and blue wavelength profiles, respectively, which are representative of the plain red, green, and blue reflectance of the dynamic scene.

Figure 27:
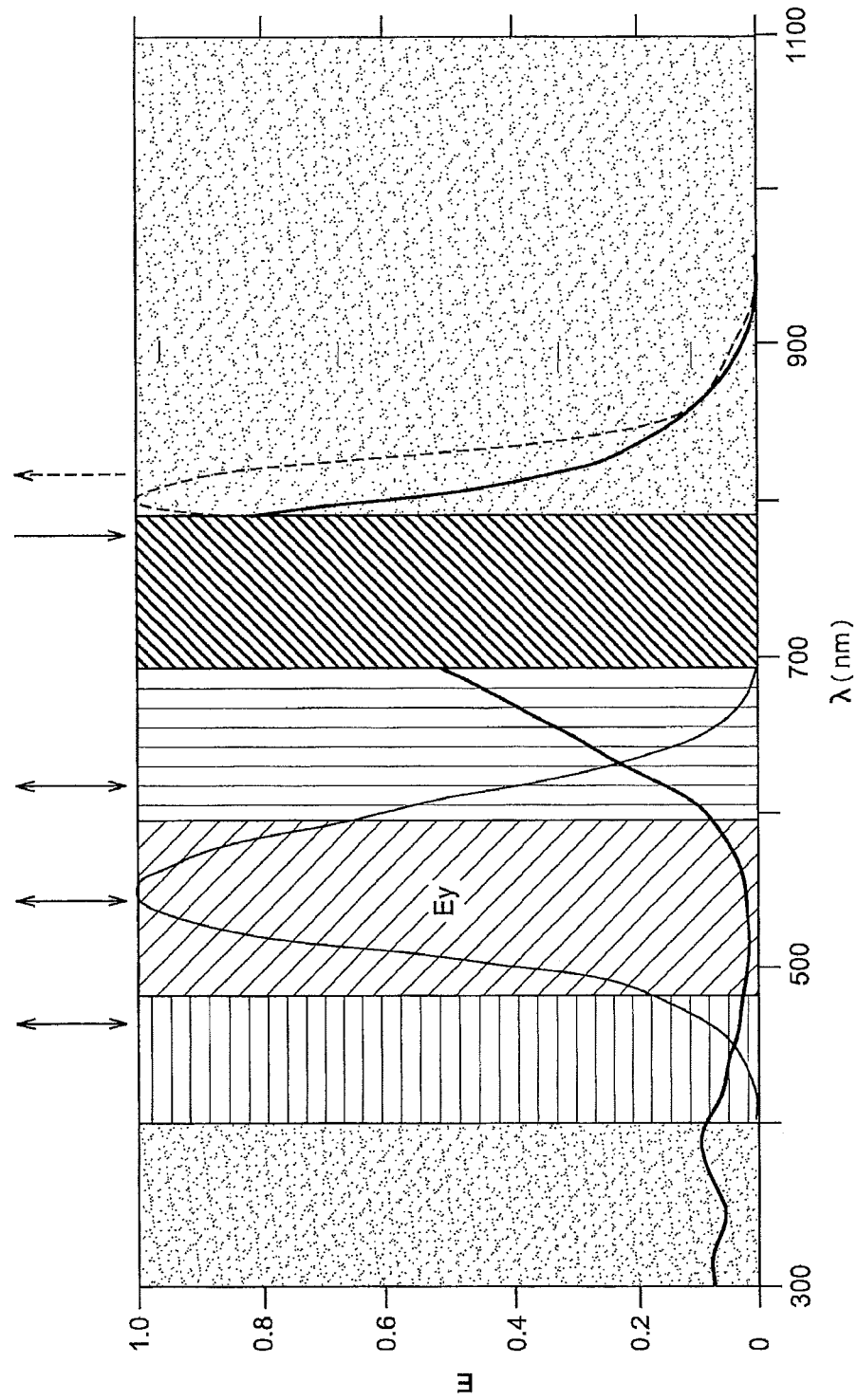
FIGS. 27 and 28 are schematic representations of embodiments of the frame-sequential multiwavelength system describing various combinations of channels.

Referring to FIG. 27, the graph represents spectra corresponding to the sensitivity of the human eye and the absorption and emission spectra of indocyanine green, respectively having peaks from left to right. The cross-hatched section in the graph represents the blocking region of an emission filter according to an embodiment of the present invention. From left to right: the first, double-ended arrow represents both a blue wavelength profile and a blue channel comprising blue reflectance image data that is transmitted by the emission filter; the second, double-ended arrow represents both a green wavelength profile and a green channel comprising green reflectance image data that is transmitted by the emission filter; the third double-ended arrow represents both a red wavelength profile and a red channel comprising red reflectance image data that is transmitted by the emission filter; the fourth, downward-pointing arrow represents a near-infrared wavelength profile that matches the excitation spectrum of indocyanine green and is blocked by the emission filter; and the fifth, upward-pointing arrow represents a near-infrared channel comprising near-infrared fluorescence image data from the indocyanine green that is transmitted by the emission filter.

Figure 28:
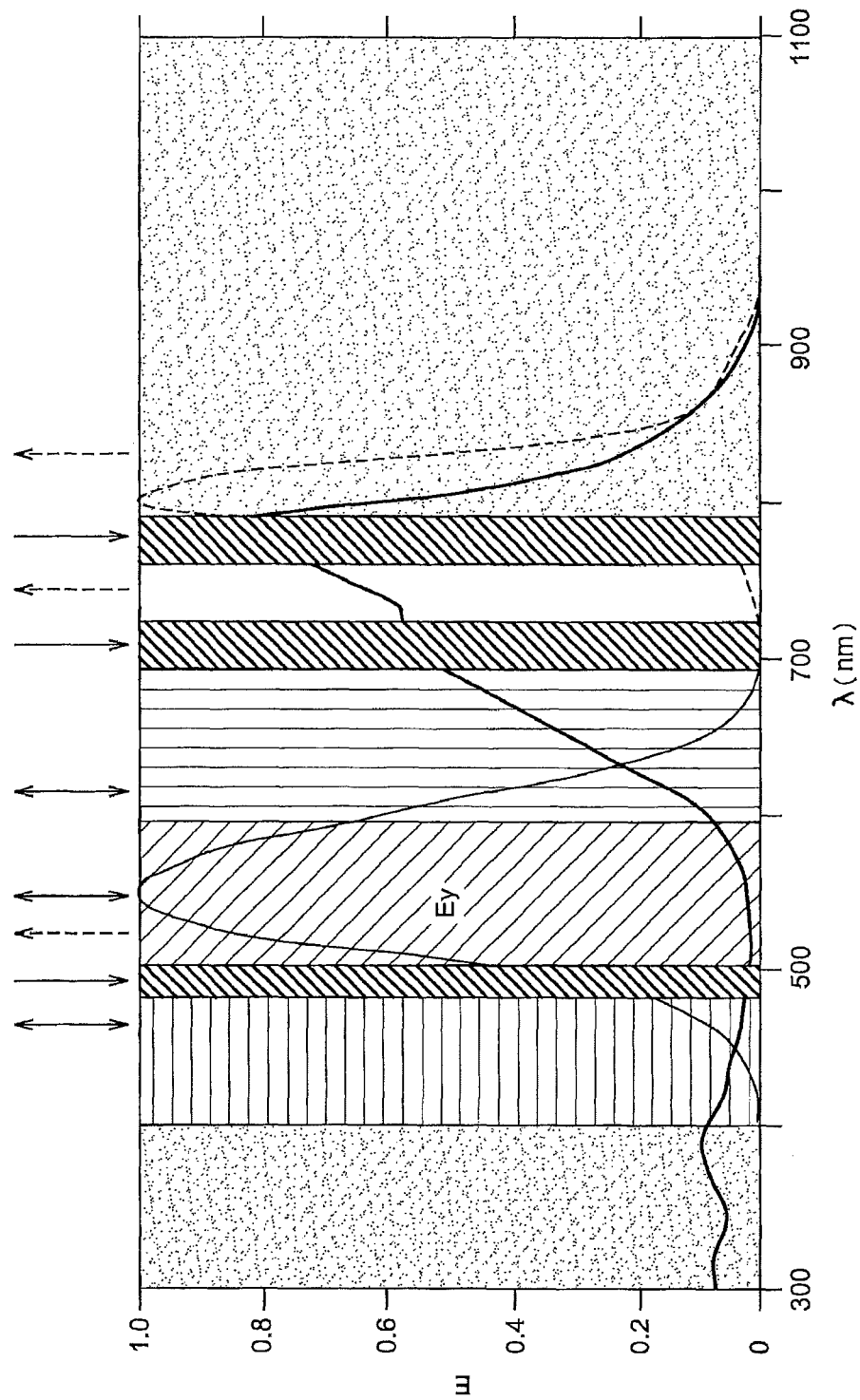

Referring to FIG. 28, the graph represents spectra corresponding to the sensitivity of the human eye and the absorption and emission spectra of indocyanine green, respectively having peaks from left to right. The cross-hatched sections in the graph represent the blocking regions of another emission filter according to one embodiment. From left to right: the first, double-ended arrow represents both a blue wavelength profile and a blue channel comprising blue reflectance image data that is transmitted by the emission filter; the second, downward-pointing arrow represents a visible wavelength profile that matches the excitation spectrum of fluorescein and is blocked by the emission filter; and the third, upward-pointing arrow represents a visible channel comprising visible fluorescence image data from the fluorescein that is transmitted by the emission filter; the fourth, double-ended arrow represents both a green wavelength profile and a green channel comprising green reflectance image data that is transmitted by the emission filter; the fifth double-ended arrow represents both a red wavelength profile and a red channel comprising red reflectance image data that is transmitted by the emission filter; the sixth, downward-pointing arrow represents a first near-infrared wavelength profile that matches the excitation spectrum of IR700 dye sold by LI-COR and is blocked by the emission filter; and the seventh, upward-pointing arrow represents a first near-infrared channel comprising near-infrared fluorescence image data from the IR700 dye that is transmitted by the emission filter; the eighth, downward-pointing arrow represents a second near-infrared wavelength profile that matches the excitation spectrum of indocyanine green and is blocked by the emission filter; and the ninth, upward-pointing arrow represents a second near-infrared channel comprising near-infrared fluorescence image data from the indocyanine green that is transmitted by the emission filter.

Another embodiment of the present invention involves a wavelength switching device that is synchronized with a pulsed laser or pulsed supercontinuum light source directed toward the dynamic scene, whereby the pulsed laser or pulsed supercontinuum light source is actuated while the wavelength switching device is idle. The pulsed laser or pulsed supercontinuum light source enables time resolved fluorescence imaging, for example to measure fluorescence lifetime or time-of-flight for tomographic reconstruction.

While the present invention has been described in connection with various embodiments, many modifications will be readily apparent to those skilled in the art. Accordingly, embodiments of the invention are not limited to the above described embodiments and examples, but instead are defined by the appended claims in light of their full scope of equivalents.

The invention claimed is:

1. A frame-sequential multiwavelength imaging system, comprising:
    a wavelength switching device comprising a plurality of light sources, the light sources producing a repeated series of different wavelength profiles, each wavelength profile being sequentially applied to a dynamic scene, the repeated series having a period of repetition, wherein the plurality of light sources produces at least one wavelength profile within each of a range of visible wavelength profiles and a range of near-infrared wavelength profiles, and wherein the fraction of the period of repetition that the at least one wavelength profile within the range of near-infrared wavelength profiles is applied is greater than the fraction of the period of repetition that the at least one wavelength profile within the range of visible wavelength profiles is applied;
    a detector that operates to detect a field of view of the dynamic scene and produce a dynamic output signal, the dynamic output signal comprising sequential frames, the sequential frames comprising image data representing the dynamic scene and corresponding to the repeated series of different wavelength profiles, the sequential frames further corresponding to a series of exposures of the detector to the dynamic scene, each exposure having a time interval between a start time and a stop time; and
    a signal processing unit, connected to the detector, for synthesizing a dynamic multiwavelength image of the dynamic scene, the dynamic multiwavelength image comprising a plurality of channels, each channel comprising image data corresponding to a different wavelength profile, the signal processing unit comprising:
        at least one input device that receives the dynamic output signal from the detector;
        at least one logic device that processes the sequential frames; and
        at least one output device that relays the dynamic multiwavelength image to at least one of a dynamic multiwavelength image display device and a dynamic multiwavelength image recording device.

2. The system of claim 1, wherein the plurality of light sources produces wavelength profiles within a range of ultraviolet wavelength profiles.

3. The system of claim 1, wherein the wavelength profiles within the range of visible wavelength profiles comprise at least a red wavelength profile, a green wavelength profile, and a blue wavelength profile.

4. The system of claim 1, wherein the detector comprises an emission filter that blocks the at least one wavelength profile within the range of near-infrared wavelength profiles and transmits light having wavelengths longer than the at least one wavelength profile within the range of near-infrared wavelength profiles.

5. The system of claim 1, wherein the fraction of the period of repetition that the at least one wavelength profile within the range of near-infrared wavelength profiles is applied is 2 to 200 times greater than the fraction of the period of repetition that the at least one wavelength profile within the range of visible wavelength profiles is applied.

6. The system of claim 1, wherein the fraction of the period of repetition that the at least one wavelength profile within the range of near-infrared wavelength profiles is applied is 10 to 50 times greater than the fraction of the period of repetition that the at least one wavelength profile within the range of visible wavelength profiles is applied.

7. The system of claim 3, wherein the fraction of the period of repetition that the at least one wavelength profile within the range of near-infrared wavelength profiles is applied is greater than the fraction of the period of repetition that the combination of the red wavelength profile, the green wavelength profile and the blue wavelength profile are applied.

8. The system of claim 3, wherein the fraction of the period of repetition that the at least one wavelength profile within the range of near-infrared wavelength profiles is applied is 2 to 200 times greater than the fraction of the period of repetition that the combination of the red wavelength profile, the green wavelength profile and the blue wavelength profile are applied.

9. The system of claim 3, wherein the fraction of the period of repetition that the at least one wavelength profile within the range of near-infrared wavelength profiles is applied is 10 to 50 times greater than the fraction of the period of repetition that the combination of the red wavelength profile, the green wavelength profile and the blue wavelength profile are applied.

10. The system of claim 3, further comprising a plurality of auxiliary light sources, the plurality of auxiliary light sources comprising at least:
    a first auxiliary light source positioned for ambient lighting beyond the field of view of the detector, the first auxiliary light source producing the red wavelength profile synchronously with the light source from the wavelength switching device that produces the red wavelength profile;
    a second auxiliary light source positioned for ambient lighting beyond the field of view of the detector, the first auxiliary light source producing the green wavelength profile synchronously with the light source from the wavelength switching device that produces the green wavelength profile; and a third auxiliary light source positioned for ambient lighting beyond the field of view of the detector, the first auxiliary light source producing the blue wavelength profile synchronously with the light source from the wavelength switching device that produces the blue wavelength profile.

11. The system of claim 3, wherein the display device displays:
the channel comprising image data corresponding to the red wavelength profile in a red display channel;
the channel comprising image data corresponding to the green wavelength profile in a green display channel;
the channel comprising image data corresponding to the blue wavelength profile in a blue display channel; and
at least one channel comprising image data corresponding to at least one near-infrared wavelength profile in a pseudo-color display channel, wherein the display device overlays the pseudo-color channel onto a full color composite of the red, blue, and green display channels.

12. The system of claim 1, further comprising at least one auxiliary light source positioned for ambient lighting beyond the field of view of the detector, the at least one auxiliary light source producing one of the different wavelength profiles synchronously with at least one light source from the wavelength switching device that produces the same one of the different wavelength profiles produced by the at least one auxiliary light source.

13. The system of claim 1, the wavelength switching device further comprising at least one illumination spectral filtration system inserted in an optical path between the plurality of light sources and the dynamic scene, the at least one illumination spectral filtration system producing the repeated series of different wavelength profiles.

14. The system of claim 1, the wavelength switching device further comprising at least one detection spectral filtration system inserted in an optical path between the dynamic scene and the detector, the at least one detection spectral filtration system producing the repeated series of different wavelength profiles.

15. The system of claim 1, wherein members of the plurality of light sources producing at least one wavelength profile within the range of visible wavelength profiles are part of a first ring light and members of the plurality of light sources producing at least one wavelength profile within the range of near-infrared wavelength profiles are part of a second ring light.

16. The system of claim 1, wherein:
the repeated series of different wavelength profiles is further capable of temporary interruption by a photographic series of wavelength profiles, the photographic series of wavelength profiles comprising at least one of the different wavelength profiles of the repeated series; and
the detector is further capable of producing a photographic output signal, the photographic output signal comprising sequential frames, the sequential frames comprising image data representing a photograph of the dynamic scene and corresponding to the photographic series of wavelength profiles, the sequential frames further corresponding to a series of exposures of the detector to the dynamic scene, each exposure having a time interval between a start time and a stop time.

17. The system of claim 1, wherein the detector comprises at least one camera for image guided surgery.

18. The system of claim 17, wherein the at least one camera comprises a stereoscopic pair of cameras.

19. A frame-sequential multiwavelength imaging system, comprising:
a wavelength switching device comprising a plurality of light sources, the light sources producing a repeated series of different wavelength profiles, each wavelength profile being sequentially applied to a dynamic scene, the repeated series having a period of repetition;
a detector that operates to detect a field of view of the dynamic scene and produce a dynamic output signal, the dynamic output signal comprising sequential frames, the sequential frames comprising image data representing the dynamic scene and corresponding to the repeated series of different wavelength profiles, the sequential frames further corresponding to a series of exposures of the detector to the dynamic scene, each exposure having a time interval between a start time and a stop time;
at least one auxiliary light source positioned for ambient lighting beyond the field of view of the detector, the at least one auxiliary light source producing one of the different wavelength profiles synchronously with at least one light source from the wavelength switching device that produces the same one of the different wavelength profiles produced by the at least one auxiliary light source; and
a signal processing unit, connected to the detector, for synthesizing a dynamic multiwavelength image of the dynamic scene, the dynamic multiwavelength image comprising a plurality of channels, each channel comprising image data corresponding to a different wavelength profile, the signal processing unit comprising:
at least one input device that receives the dynamic output signal from the detector;
at least one logic device that processes the sequential frames; and
at least one output device that relays the dynamic multiwavelength image to at least one of a dynamic multiwavelength image display device and a dynamic multiwavelength image recording device.

20. A frame-sequential multiwavelength imaging system, comprising:
a wavelength switching device comprising a plurality of light sources, the light sources producing a repeated series of different wavelength profiles, each wavelength profile being sequentially applied to a dynamic scene, the repeated series having a period of repetition, wherein the plurality of light sources produces wavelength profiles within a range of visible wavelength profiles, a range of near-infrared wavelength profiles, or a range of ultraviolet wavelength profiles, and wherein the fraction of the period of repetition that at least one of the produced wavelength profiles is applied is greater than the fraction of the period of repetition that another of the produced wavelength profiles is applied;
a detector that operates to detect a field of view of the dynamic scene and produce a dynamic output signal, the dynamic output signal comprising sequential frames, the sequential frames comprising image data representing the dynamic scene and corresponding to the repeated series of different wavelength profiles, the sequential frames further corresponding to a series of exposures of the detector to the dynamic scene, each exposure having a time interval between a start time and a stop time; and
a signal processing unit, connected to the detector, for synthesizing a dynamic multiwavelength image of the dynamic scene, the dynamic multiwavelength image comprising a plurality of channels, each channel comprising image data corresponding to a different wavelength profile, the signal processing unit comprising:

at least one input device that receives the dynamic output signal from the detector;

at least one logic device that processes the sequential frames; and at least one output device that relays the dynamic multiwavelength image to at least one of a dynamic multiwavelength image display device and a dynamic multiwavelength image recording device.

* * * * *